United States Patent
Lee et al.

(10) Patent No.: US 7,510,531 B2
(45) Date of Patent: Mar. 31, 2009

(54) SYSTEM AND METHOD FOR DISCRIMINATION OF CENTRAL AND OBSTRUCTIVE DISORDERED BREATHING EVENTS

(75) Inventors: Kent Lee, Fridley, MN (US); John D. Hatlestad, Maplewood, MN (US); Qingsheng Zhu, Little Canada, MN (US); Jeffrey E. Stahmann, Ramsey, MN (US); Jesse W. Hartley, Lino Lakes, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 556 days.

(21) Appl. No.: 10/824,776

(22) Filed: Apr. 15, 2004

(65) Prior Publication Data

US 2005/0074741 A1   Apr. 7, 2005

Related U.S. Application Data

(60) Provisional application No. 60/504,722, filed on Sep. 18, 2003.

(51) Int. Cl.
*A61B 5/08* (2006.01)
(52) U.S. Cl. .................... 600/534; 600/529
(58) Field of Classification Search .......... 600/529–543
See application file for complete search history.

(56) References Cited

U.S. PATENT DOCUMENTS

| | | |
|---|---|---|
| 4,365,636 A | 12/1982 | Barker |
| 4,562,841 A | 1/1986 | Brockway et al. |
| 4,702,253 A | 10/1987 | Nappholz et al. |
| 4,721,110 A | 1/1988 | Lampadius |
| 4,777,962 A | 10/1988 | Watson et al. |
| 4,802,485 A | 2/1989 | Bowers et al. |
| 4,807,629 A | 2/1989 | Baudino et al. |
| 4,813,427 A | 3/1989 | Schlaefke et al. |
| 4,827,935 A | 5/1989 | Geddes et al. |
| 4,830,008 A | 5/1989 | Meer |
| 4,836,219 A | 6/1989 | Hobson et al. |
| 4,856,524 A | 8/1989 | Baker, Jr. |
| 4,886,064 A | 12/1989 | Strandberg |

(Continued)

FOREIGN PATENT DOCUMENTS

EP   0750920   1/1997

(Continued)

OTHER PUBLICATIONS

Balaban et al., *Feasibility of Screening for Sleep Apnea Using Pacemaker Impedance Sensor*, NASPE (2001).

(Continued)

*Primary Examiner*—Max Hindenburg
*Assistant Examiner*—Karen E Toth
(74) *Attorney, Agent, or Firm*—Hollingsworth & Funk, LLC

(57) ABSTRACT

Disordered breathing events may be classified as central, obstructive or a combination of central an obstructive in origin based on patient motion associated with respiratory effort. Central disordered breathing is associated with disrupted respiration with reduced respiratory effort. Obstructive disordered breathing is associated with disrupted respiration accompanied by respiratory effort. A disordered breathing classification system includes a disordered breathing detector and a respiratory effort motion sensor. Components of the disordered breathing classification system may be fully or partially implantable.

77 Claims, 22 Drawing Sheets

U.S. PATENT DOCUMENTS

| | | |
|---|---|---|
| 4,928,688 A | 5/1990 | Mower |
| 4,958,632 A | 9/1990 | Duggan |
| 4,972,842 A | 11/1990 | Korten et al. |
| 5,010,888 A | 4/1991 | Jadvar et al. |
| 5,024,222 A | 6/1991 | Thacker |
| 5,036,849 A | 8/1991 | Hauck et al. |
| 5,047,930 A | 9/1991 | Martens et al. |
| 5,063,927 A | 11/1991 | Webb et al. |
| 5,105,354 A | 4/1992 | Nishimura |
| 5,123,425 A | 6/1992 | Shannon, Jr. et al. |
| 5,146,918 A | 9/1992 | Kallok et al. |
| 5,156,157 A | 10/1992 | Valenta, Jr. et al. |
| 5,178,156 A | 1/1993 | Takishima et al. |
| 5,187,657 A | 2/1993 | Forbes |
| 5,188,106 A | 2/1993 | Nappholz et al. |
| 5,203,348 A | 4/1993 | Dahl et al. |
| 5,211,173 A | 5/1993 | Kallok et al. |
| 5,215,082 A | 6/1993 | Kallok et al. |
| 5,230,337 A | 7/1993 | Dahl et al. |
| 5,233,983 A | 8/1993 | Markowitz |
| 5,243,979 A | 9/1993 | Stein et al. |
| 5,245,995 A | 9/1993 | Sullivan et al. |
| 5,275,159 A | 1/1994 | Griebel |
| 5,280,791 A | 1/1994 | Lavie |
| 5,284,136 A | 2/1994 | Hauck et al. |
| 5,299,118 A | 3/1994 | Martens et al. |
| 5,301,677 A | 4/1994 | Hsung |
| 5,313,953 A | 5/1994 | Yomtov et al. |
| 5,318,597 A | 6/1994 | Hauck et al. |
| 5,334,222 A | 8/1994 | Salo et al. |
| 5,335,657 A | 8/1994 | Terry, Jr. et al. |
| 5,360,442 A | 11/1994 | Dahl et al. |
| 5,366,496 A | 11/1994 | Dahl et al. |
| 5,376,476 A | 12/1994 | Eylon |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,404,877 A | 4/1995 | Nolan et al. |
| 5,411,031 A | 5/1995 | Yomtov |
| 5,466,245 A | 11/1995 | Heemels et al. |
| 5,483,969 A | 1/1996 | Testerman et al. |
| 5,485,851 A | 1/1996 | Erickson |
| 5,487,755 A | 1/1996 | Snell et al. |
| 5,520,176 A | 5/1996 | Cohen |
| 5,522,862 A | 6/1996 | Testerman et al. |
| 5,540,727 A | 7/1996 | Tockman et al. |
| 5,540,732 A | 7/1996 | Testerman |
| 5,540,734 A | 7/1996 | Zabara |
| 5,545,186 A | 8/1996 | Olson et al. |
| 5,545,202 A | 8/1996 | Dahl et al. |
| 5,549,655 A | 8/1996 | Erickson |
| 5,591,216 A | 1/1997 | Testerman et al. |
| 5,593,431 A | 1/1997 | Sheldon |
| 5,603,732 A | 2/1997 | Dahl et al. |
| 5,622,178 A | 4/1997 | Gilham |
| 5,632,281 A | 5/1997 | Rayburn |
| 5,645,570 A | 7/1997 | Corbucci |
| 5,697,951 A | 12/1997 | Harpstead et al. |
| 5,704,345 A | 1/1998 | Berthon-Jones |
| 5,713,933 A | 2/1998 | Condie et al. |
| 5,716,377 A | 2/1998 | Rise et al. |
| 5,720,771 A | 2/1998 | Snell |
| 5,738,102 A | 4/1998 | Lemelson |
| 5,792,188 A | 8/1998 | Starkweather et al. |
| 5,794,615 A | 8/1998 | Estes |
| 5,802,188 A | 9/1998 | McDonough |
| 5,814,087 A | 9/1998 | Renirie |
| 5,836,987 A | 11/1998 | Baumann et al. |
| 5,844,680 A | 12/1998 | Sperling |
| 5,855,593 A | 1/1999 | Olson et al. |
| 5,861,011 A | 1/1999 | Stoop |
| 5,876,353 A | 3/1999 | Riff |
| 5,891,023 A | 4/1999 | Lynn |
| 5,902,250 A | 5/1999 | Verrier et al. |
| 5,911,218 A | 6/1999 | DiMarco |
| 5,916,243 A | 6/1999 | KenKnight et al. |
| 5,944,680 A * | 8/1999 | Christopherson et al. ..... 602/42 |
| 5,957,861 A | 9/1999 | Combs et al. |
| 5,964,778 A | 10/1999 | Fugoso et al. |
| 5,970,975 A | 10/1999 | Estes et al. |
| 5,974,340 A | 10/1999 | Kadhiresan |
| 5,974,349 A | 10/1999 | Levine |
| 5,981,011 A | 11/1999 | Overcash et al. |
| 6,021,351 A | 2/2000 | Kadhiresan et al. |
| 6,026,320 A | 2/2000 | Carlson et al. |
| 6,044,297 A | 3/2000 | Sheldon et al. |
| 6,044,298 A | 3/2000 | Salo et al. |
| 6,055,454 A | 4/2000 | Heemels |
| 6,059,725 A | 5/2000 | Steinschneider |
| 6,064,910 A | 5/2000 | Andersson et al. |
| 6,076,015 A | 6/2000 | Hartley et al. |
| 6,091,973 A | 7/2000 | Colla et al. |
| 6,091,986 A | 7/2000 | Keimel |
| 6,099,479 A | 8/2000 | Christopherson et al. |
| 6,120,441 A | 9/2000 | Griebel |
| 6,126,611 A | 10/2000 | Bourgeois et al. |
| 6,128,534 A | 10/2000 | Park et al. |
| 6,132,384 A | 10/2000 | Christopherson et al. |
| 6,141,581 A | 10/2000 | Olson et al. |
| 6,141,590 A | 10/2000 | Renirie et al. |
| 6,148,814 A | 11/2000 | Clemmer et al. |
| 6,181,961 B1 | 1/2001 | Prass |
| 6,190,326 B1 | 2/2001 | McKinnon et al. |
| 6,200,265 B1 | 3/2001 | Walsh et al. |
| 6,212,435 B1 | 4/2001 | Lattner et al. |
| 6,221,011 B1 | 4/2001 | Bardy |
| 6,240,316 B1 | 5/2001 | Richmond et al. |
| 6,251,126 B1 | 6/2001 | Ottenhoff et al. |
| 6,258,039 B1 | 7/2001 | Okamoto et al. |
| 6,259,947 B1 | 7/2001 | Olson et al. |
| 6,263,244 B1 | 7/2001 | Mann et al. |
| 6,264,606 B1 | 7/2001 | Ekwall et al. |
| 6,269,269 B1 | 7/2001 | Ottenhoff et al. |
| 6,270,457 B1 | 8/2001 | Bardy |
| 6,272,377 B1 | 8/2001 | Sweeney et al. |
| 6,275,727 B1 | 8/2001 | Hopper et al. |
| 6,277,072 B1 | 8/2001 | Bardy |
| 6,280,380 B1 | 8/2001 | Bardy |
| 6,285,907 B1 | 9/2001 | Kramer et al. |
| 6,286,508 B1 | 9/2001 | Remmers et al. |
| 6,303,270 B1 | 10/2001 | Flaim et al. |
| 6,306,088 B1 | 10/2001 | Krausman |
| 6,310,085 B1 | 10/2001 | Willis |
| 6,312,378 B1 | 11/2001 | Bardy |
| 6,336,903 B1 | 1/2002 | Bardy |
| 6,351,669 B1 | 2/2002 | Hartley et al. |
| 6,351,670 B1 | 2/2002 | Kroll |
| 6,353,759 B1 | 3/2002 | Hartley et al. |
| 6,358,203 B2 | 3/2002 | Bardy |
| 6,360,127 B1 | 3/2002 | Ding et al. |
| 6,361,494 B1 | 3/2002 | Lindenthaler |
| 6,363,270 B1 | 3/2002 | Colla et al. |
| 6,366,813 B1 | 4/2002 | DiLorenzo |
| 6,368,284 B1 | 4/2002 | Bardy |
| 6,368,287 B1 | 4/2002 | Hadas |
| 6,371,922 B1 | 4/2002 | Baumann et al. |
| 6,375,621 B1 | 4/2002 | Sullivan |
| 6,375,623 B1 | 4/2002 | Gavriely |
| 6,387,907 B1 | 5/2002 | Hendricks et al. |
| 6,398,728 B1 | 6/2002 | Bardy |
| 6,411,848 B2 | 6/2002 | Kramer et al. |
| 6,411,850 B1 | 6/2002 | Kay et al. |
| 6,414,183 B1 | 7/2002 | Sakamoto et al. |
| 6,415,183 B1 | 7/2002 | Scheiner et al. |

| | | |
|---|---|---|
| 6,424,865 B1 | 7/2002 | Ding |
| 6,438,407 B1 | 8/2002 | Ousdigian et al. |
| 6,438,410 B2 | 8/2002 | Hsu et al. |
| 6,440,066 B1 | 8/2002 | Bardy |
| 6,449,503 B1 | 9/2002 | Hsu |
| 6,450,957 B1 | 9/2002 | Yoshimi |
| 6,454,719 B1 | 9/2002 | Greenhut |
| 6,459,929 B1 | 10/2002 | Hopper et al. |
| 6,467,333 B2 | 10/2002 | Lewis et al. |
| 6,480,733 B1 | 11/2002 | Turcott |
| 6,487,443 B2 | 11/2002 | Olson et al. |
| 6,527,729 B1 | 3/2003 | Turcott |
| 6,542,775 B2 | 4/2003 | Ding et al. |
| 6,547,743 B2 * | 4/2003 | Brydon .................. 600/534 |
| 6,572,543 B1 | 6/2003 | Christopherson et al. |
| 6,574,507 B1 | 6/2003 | Bonnet |
| 6,580,944 B1 | 6/2003 | Katz et al. |
| 6,589,188 B1 | 7/2003 | Street et al. |
| 6,595,928 B2 | 7/2003 | Mansy et al. |
| 6,597,951 B2 | 7/2003 | Kramer et al. |
| 6,600,949 B1 | 7/2003 | Turcott |
| 6,641,542 B2 | 11/2003 | Cho et al. |
| 6,658,292 B2 | 12/2003 | Kroll et al. |
| 6,662,032 B1 | 12/2003 | Gavish et al. |
| 6,694,186 B2 | 2/2004 | Bardy |
| 6,704,590 B2 | 3/2004 | Haldeman |
| 6,708,058 B2 | 3/2004 | Kim et al. |
| 6,731,984 B2 | 5/2004 | Cho et al. |
| 6,741,885 B1 | 5/2004 | Park et al. |
| 6,748,252 B2 | 6/2004 | Lynn et al. |
| 6,752,765 B1 | 6/2004 | Jensen et al. |
| 6,752,766 B2 | 6/2004 | Kowallik et al. |
| 6,773,404 B2 | 8/2004 | Poezevera et al. |
| 6,810,287 B2 | 10/2004 | Zhu et al. |
| 6,830,548 B2 | 12/2004 | Bonnet et al. |
| 6,881,192 B1 | 4/2005 | Park |
| 6,890,306 B2 | 5/2005 | Poezevera |
| 6,892,095 B2 | 5/2005 | Salo |
| 6,904,320 B2 | 6/2005 | Park et al. |
| 6,910,481 B2 | 6/2005 | Kimmel et al. |
| 6,928,324 B2 | 8/2005 | Park et al. |
| 6,964,641 B2 * | 11/2005 | Cho et al. ................ 600/529 |
| 6,988,498 B2 | 1/2006 | Berthon-Jones et al. |
| 7,025,729 B2 | 4/2006 | de Chazal et al. |
| 7,027,871 B2 | 4/2006 | Burnes et al. |
| 7,039,468 B2 | 5/2006 | Freed et al. |
| 7,062,308 B1 | 6/2006 | Jackson |
| 7,081,095 B2 | 7/2006 | Lynn et al. |
| 7,089,936 B2 | 8/2006 | Madaus et al. |
| 7,092,755 B2 | 8/2006 | Florio |
| 7,130,687 B2 | 10/2006 | Cho et al. |
| 7,136,704 B2 | 11/2006 | Schulman |
| 7,155,278 B2 | 12/2006 | King et al. |
| 7,184,817 B2 | 2/2007 | Zhu et al. |
| 7,189,204 B2 | 3/2007 | Ni et al. |
| 7,194,313 B2 | 3/2007 | Libbus |
| 7,207,945 B2 | 4/2007 | Bardy |
| 7,225,013 B2 | 5/2007 | Geva et al. |
| 7,225,021 B1 | 5/2007 | Park et al. |
| 7,225,809 B1 | 6/2007 | Bowen et al. |
| 7,231,250 B2 | 6/2007 | Band et al. |
| 7,252,640 B2 | 8/2007 | Ni et al. |
| 7,269,459 B1 | 9/2007 | Koh |
| 7,302,295 B2 | 11/2007 | Stahmann et al. |
| 2001/0000346 A1 | 4/2001 | Ruton et al. |
| 2001/0018547 A1 | 8/2001 | Mechlenburg et al. |
| 2001/0031930 A1 | 10/2001 | Roizen et al. |
| 2002/0082652 A1 | 6/2002 | Wentkowski et al. |
| 2002/0143264 A1 | 10/2002 | Ding et al. |
| 2002/0169384 A1 | 11/2002 | Kowallik et al. |
| 2002/0169485 A1 | 11/2002 | Pless et al. |
| 2002/0193685 A1 | 12/2002 | Mate et al. |
| 2002/0193697 A1 | 12/2002 | Cho et al. |
| 2002/0193839 A1 | 12/2002 | Cho et al. |
| 2003/0023184 A1 | 1/2003 | Pitts-Crick et al. |
| 2003/0050538 A1 | 3/2003 | Naghavi et al. |
| 2003/0055348 A1 | 3/2003 | Chazal et al. |
| 2003/0055461 A1 | 3/2003 | Girouard et al. |
| 2003/0060848 A1 | 3/2003 | Kieval et al. |
| 2003/0073919 A1 | 4/2003 | Hampton et al. |
| 2003/0083241 A1 | 5/2003 | Young |
| 2003/0088027 A1 | 5/2003 | Chin et al. |
| 2003/0100925 A1 | 5/2003 | Pape et al. |
| 2003/0105497 A1 | 6/2003 | Zhu et al. |
| 2003/0121519 A1 | 7/2003 | Estes et al. |
| 2003/0139780 A1 | 7/2003 | Markowitz et al. |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171687 A1 | 9/2003 | Irie et al. |
| 2003/0178031 A1 | 9/2003 | Du Pen et al. |
| 2003/0187336 A1 | 10/2003 | Odagiri et al. |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2003/0209246 A1 | 11/2003 | Schroeder et al. |
| 2003/0216789 A1 | 11/2003 | Deem et al. |
| 2004/0002742 A1 | 1/2004 | Florio |
| 2004/0030362 A1 | 2/2004 | Hill et al. |
| 2004/0039605 A1 | 2/2004 | Bardy |
| 2004/0059240 A1 * | 3/2004 | Cho et al. ................ 600/532 |
| 2004/0073093 A1 | 4/2004 | Hatlestad |
| 2004/0088027 A1 | 5/2004 | Burnes et al. |
| 2004/0102814 A1 | 5/2004 | Sorensen et al. |
| 2004/0111040 A1 | 6/2004 | Ni et al. |
| 2004/0116981 A1 | 6/2004 | Mazar |
| 2004/0122487 A1 | 6/2004 | Hatlestad et al. |
| 2004/0122488 A1 | 6/2004 | Mazar et al. |
| 2004/0128161 A1 | 7/2004 | Mazar et al. |
| 2004/0133079 A1 | 7/2004 | Mazar et al. |
| 2004/0138719 A1 | 7/2004 | Cho et al. |
| 2004/0163648 A1 | 8/2004 | Burton |
| 2004/0176695 A1 * | 9/2004 | Poezevara ................ 600/513 |
| 2004/0176809 A1 | 9/2004 | Cho et al. |
| 2004/0186523 A1 | 9/2004 | Florio |
| 2004/0210154 A1 | 10/2004 | Kline |
| 2004/0210155 A1 | 10/2004 | Takemura et al. |
| 2004/0210261 A1 | 10/2004 | King et al. |
| 2004/0215240 A1 | 10/2004 | Lovett et al. |
| 2004/0230229 A1 | 11/2004 | Lovett et al. |
| 2004/0230230 A1 | 11/2004 | Lindstrom |
| 2004/0249416 A1 | 12/2004 | Yun et al. |
| 2005/0004615 A1 | 1/2005 | Sanders |
| 2005/0039745 A1 | 2/2005 | Stahmann et al. |
| 2005/0042589 A1 | 2/2005 | Hatlestad et al. |
| 2005/0043644 A1 | 2/2005 | Stahmann et al. |
| 2005/0043652 A1 | 2/2005 | Lovett et al. |
| 2005/0043772 A1 | 2/2005 | Stahmann et al. |
| 2005/0061315 A1 | 3/2005 | Lee et al. |
| 2005/0065447 A1 * | 3/2005 | Lee et al. ................ 600/529 |
| 2005/0065567 A1 | 3/2005 | Lee et al. |
| 2005/0065572 A1 | 3/2005 | Hartley et al. |
| 2005/0085865 A1 * | 4/2005 | Tehrani ................... 607/42 |
| 2005/0101841 A9 | 5/2005 | Kaylor et al. |
| 2005/0107838 A1 * | 5/2005 | Lovett et al. ............. 607/17 |
| 2005/0119711 A1 | 6/2005 | Cho et al. |
| 2005/0142070 A1 | 6/2005 | Hartley et al. |
| 2005/0145246 A1 | 7/2005 | Hartley et al. |
| 2005/0159784 A1 | 7/2005 | Arceta |
| 2005/0240240 A1 | 10/2005 | Park et al. |
| 2005/0288728 A1 | 12/2005 | Libbus et al. |
| 2006/0047333 A1 | 3/2006 | Tockman et al. |
| 2006/0293714 A1 | 12/2006 | Salo et al. |
| 2007/0005114 A1 | 1/2007 | Salo et al. |

| | | | |
|---|---|---|---|
| 2007/0112388 A1 | 5/2007 | Salo | |
| 2007/0150014 A1 | 6/2007 | Kramer et al. | |
| 2007/0161873 A1 | 7/2007 | Ni et al. | |
| 2007/0282215 A1 | 12/2007 | Ni et al. | |

FOREIGN PATENT DOCUMENTS

| | | |
|---|---|---|
| EP | 0 940 155 A | 8/1999 |
| EP | 1 151 718 A | 7/2001 |
| EP | 1162125 | 12/2001 |
| EP | 1 172 125 A1 | 1/2002 |
| WO | WO8402080 | 6/1984 |
| WO | WO9203983 | 3/1992 |
| WO | 99/04841 | 2/1999 |
| WO | WO9904841 | 2/1999 |
| WO | WO 00/01438 A | 1/2000 |
| WO | WO 00/17615 | 3/2000 |
| WO | WO0017615 | 3/2000 |
| WO | 02/087696 | 7/2002 |
| WO | WO03075744 | 9/2003 |
| WO | WO2004062485 | 7/2004 |
| WO | WO2005028029 | 3/2005 |

OTHER PUBLICATIONS

Bradley et al., Pathophysiologic and Therapeutic Implications of Sleep Apnea in Congestive Heart Failure, 3 J. Cardiac Failure 223-240 (1996). Abstract only.
Bradley et al., Sleep Apnea and Heart Failure, Park I: Obstructive Sleep Apnea, 107 Circulation 1671-1678 (2003).
Garrigue et al., Night Atrial Overdrive with DDD Pacing Results in a Significant Reduction of Sleep Apnea Episodes and QOL Improvement in Heart Failure Patients, NASPE (2001).
Garrigue et al., Benefit of Atrial Pacing in Sleep Apnea Syndrome, 346 N. Engl. J. Med. 404-412 (2002). Abstract only.
Hilton et al., Evaluation of Frequency and Time-frequency Spectral Analysis of Heart Rate Variability as a Diagnostic Marker of the Sleep Apnea Syndrome, 37 Med. Biol. Eng. Comput. 760-769 (1999). Abstract only.
Jais et al., Night Atrial Overdrive with DDD Pacing: a New Therapy for Sleep Apnea Syndrome, NASPE (2000).
Javaheri et al., Sleep Apnea in 81 Ambulatory Male Patients with Stable Heart Failure: Types and Their Prevalences, Consequences, and Presentations, 97 Circulation 2154-2159 (1998).
Olusola et al., Nightcap: Laboratory and home-based evaluation of a portable sleep monitor, 32 Psychophysiology, 32-98 (1995). Abstract only.
Verrier et al., Sleep, dreams, and sudden death: the case for sleep as an autonomic stress test for the heart, 31 Cardiovascular Research 181-211 (1996).
Verrier et al., Sleep Related Cardiovascular Risk: New Home-Based Monitoring Technology for Improved Diagnosis and Therapy, 2 A.N.E. 158-175 (1997).

Roche et al., Screening of Obstructive Sleep Apnea Syndrome by Heart Rate Variability Analysis, 100 Circulation 1411-1455 (1999).
Shahrokh, A Mechanism of Central Sleep Apnea In Patients With Heart Failure,341 N. Engl. J. Med. 949-954 (1999). Abstract only.
Vanninen et al., Cardiac Sympathovagal Balance During Sleep Apnea Episodes, 16 Clin. Physiol. 209-216 (1996). Abstract only.
Waldermark et al., Detection of Apnea using Short Window FFT Technique and Artificial Neural Network, 3390 SPIE International Society for Optical Engineering 122-133 (1998).
Young et al., The Occurrence of Sleep-Disordered Breathing Among Middle Aged Adults, N. Engl. J. Med. 1230-1235 (1993). Abstract only.
Holger Steltner et al., *Diagnosis of Sleep Apnea by Automatic Analysis of Nasal Pressure and Forced Oscillation Impedance*. Am. Journal Respiratory Critical Care Medicine, vol. 165, pp. 940-944 (2002).
Aircraft Noise and Sleep Disturbance: Final Report, prepared by the Civil Aviation Authority London on behalf of the Department of Trade, Aug. 1980 (CAA Report).
Coleridge et al. "The distribution, connexions and histology of baroreceptors in the pulmonary artery, with some observations on the sensory innervation of the ductus arteriosus." *Physiology*. May 1961. vol. 156, pp. 591-602.
Dark et al., Breathing Pattern Abnormalities and Arterial Oxygen Desaturation During Sleep in the Congestive Heart Failure Syndrome, Chest, Jun. 1987, 6:833-6.
Hoffman et al., Cheyne-Stokes Respiration in Patients Recovering from Acute Cardiogenic Pulmonary Edema, Chest 1990, 97:410-12.
Neil et al., Effects of electrical stimulation of the aortic nerve on blood pressure and respiration in cats and rabbits under chloralose and nembutal anaesthesia, Journal of Physiology, Sep. 1949. vol. 109 (3-4) p. 392-401.
Peters et al., Tempral and spatial summation caused by aortic nerve stimulation in rabbits. Effects of stimulation frequencies and amplitudes. Journal of the Autonomic Nervous System. 1989. vol. 27, pp. 193-205 Abstract only.
Rees et al., Paroxysmal Nocturnal Dyspnoea and Periodic Respiration, The Lancet, Dec. 22-29, 1979, pp. 1315-1317, abstract only.
Sato et al., Novel Therapeutic Strategy against Central Baroreflex Failure: A Bionic Baroreflex System, Circulation, Jul. 1999 vol. 100, pp. 299-304.
Smits et al., Defibrillation Threshold (DFT) Model of a Fully Subcutaneous ICD System, Europace Supplements, vol. 2, Jun. 2001 at col. 778, p. B83.
Steltner et al., Diagnosis of Sleep Apnea by Automatic Analysis of Nasal Pressure and Forced Oscillation Impedance. Am. Journal Respiratory Critical Care Medicine, vol. 165, pp. 940-944, 2002.
Stirbis et al., Optmizing the Shape of Implanted Artificial Pacemakers, Kaunas Medical Institute. Translated from Meditsinskaya Tekhnika, No. 6, pp. 25-27, 1986.
Thrasher et al., Unloading arterial baroreceptors causes neurogenic hypertension, American Journal Physiol. Regulatory Integrative Comp. Physiol, 2002 vol. 282, R1044-R1053.

\* cited by examiner

Trigger On Trigger Off

SYSTEM AND METHOD FOR DISCRIMINATION OF CENTRAL AND OBSTRUCTIVE DISORDERED BREATHING EVENTS

RELATED PATENT DOCUMENTS

This application claims the benefit of Provisional Patent Application Ser. No. 60/504,722, filed on Sep. 18, 2003, to which priority is claimed pursuant to 35 U.S.C. §119(e) and which is hereby incorporated herein by reference in its entirety.

FIELD OF THE INVENTION

The present invention relates generally to methods and systems for classifying disordered breathing events according to origin.

BACKGROUND OF THE INVENTION

Normal breathing occurs when the central nervous system properly functions and sends signals instructing the body to breathe and obstructions to the airway are not present. Disordered breathing occurs when a patient experiences insufficient respiration with or without respiratory effort. Disordered breathing events may be classified by origin. For example, disordered breathing can originate from a deficiency in the central nervous system (central disordered breathing) or from an obstructed airway (obstructive disordered breathing).

Central disordered breathing is caused by a disruption of the nervous system signals that control breathing. During central disordered breathing events, the patient makes no effort to breath or the respiratory effort is insufficient.

Obstructive disordered breathing generally occurs due to an obstruction of a patient's airway. For example, the patient's tongue or other soft tissue of the throat may collapse into the patient's airway. The breathing reflex is triggered, the patient attempts to breathe, but respiration is disrupted because of the occluded airway. Disordered breathing events may involve central disordered breathing, obstructive disordered breathing, or a mixture of obstructive and central types of disordered breathing.

Although episodes of disordered breathing can occur when the patient is awake, they more often occur during sleep. Sleep apnea is characterized by periods of interrupted breathing during sleep. Hypopnea is another form of disordered breathing characterized by periods of shallow breathing. Sleep apnea, hypopnea and/or other forms of disordered breathing events may be associated with central, obstructive, or mixed disordered breathing origins. Other forms of disordered breathing that may be classified according to origin may include, for example, tachypnea (rapid breathing), hyperpnea (heavy breathing), dyspnea (labored breathing), and periodic breathing (periodically waxing and waning respiration).

A severe form of disordered breathing that generally includes periods of central sleep apnea is known as Cheyne-Stokes respiration (CSR). CSR is a type of periodic breathing marked by periodic patterns of waxing and waning respiration interrupted by periods of central apnea. CSR is commonly associated with poor prognosis when diagnosing congestive heart failure (CHF) patients.

Classification of disordered breathing events by origin, e.g., central, obstructive, or mixed, may be used to enhance the diagnosis of disordered breathing. Therapy for disordered breathing and other conditions may be more effectively provided with knowledge of the origin of breathing disorders experienced by the patient.

SUMMARY OF THE INVENTION

Embodiments of the invention are directed to methods and systems for classifying the origin of disordered breathing events and/or discriminating between disordered breathing origin types. One embodiment of the invention involves a method for classifying disordered breathing in a patient. The method includes detecting a disordered breathing event and sensing motion associated with respiratory effort during he disordered breathing event. The disordered breathing event is classified based on the sensed motion. At least one of detecting the disordered breathing event, sensing the motion associated with respiratory effort, and classifying the disordered breathing event are performed at least in part implantably.

In another embodiment of the invention, a disordered breathing classification system includes a disordered breathing detector configured to detect disordered breathing in a patient. A motion sensor is configured to sense the patient's motion associated with respiratory effort during the disordered breathing event. A disordered breathing classification processor is coupled to the motion sensor and the disordered breathing detector. The disordered breathing classification processor is configured to classify the disordered breathing event based on motion associated with respiratory effort. At least one of the disordered breathing detector, the motion sensor, and the disordered breathing classification processor is at least in part implantable.

Figure 1A:
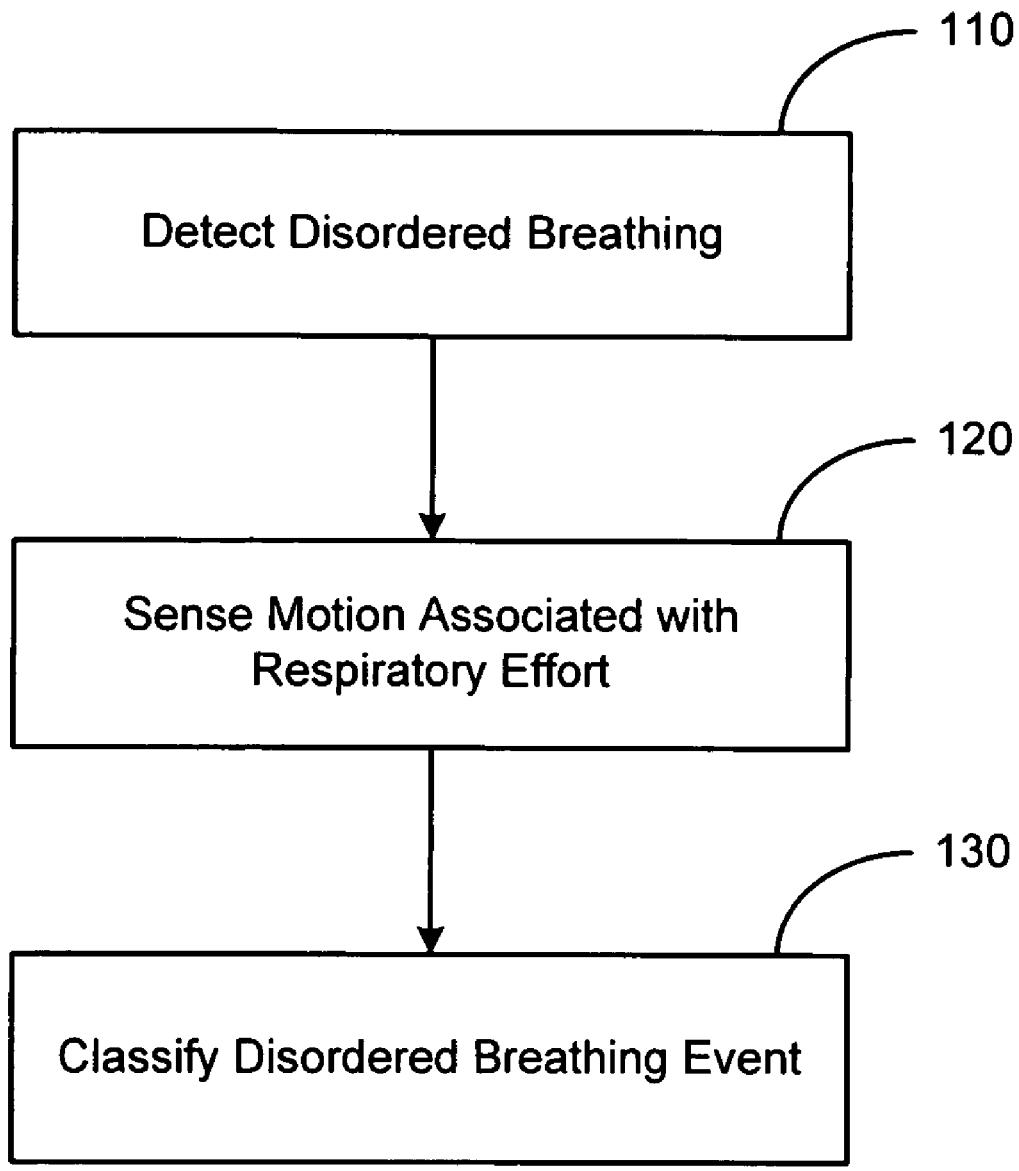
FIG. 1A is a flowchart of a method of classifying a disordered breathing event in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings that form a part hereof, and in which are shown by way of illustration, various embodiments by which the invention may be practiced. It is to be understood that other embodiments may be utilized, and structural and functional changes may be made without departing from the scope of the present invention.

Embodiments of the invention involve classifying the origin of disordered breathing events. The origin of disordered breathing events may be classified as central, obstructive, or a combination of central and obstructive origin types. According to various implementations, disordered breathing events may be classified based on a patient's motion associated with respiratory effort during the disordered breathing event. For example, central apnea may be identified by insufficient respiration for at least about 10 seconds with insufficient respiratory effort. Obstructive apnea may be identified by insufficient respiratory inspiration for at least about 10 seconds accompanied by respiratory effort. Respiratory effort may be detected by sensing patient motion associated with respiratory effort during the disordered breathing event. The sensed motion may comprise motion of the patient's chest, abdomen, diaphragm, and/or other motion associated with respiratory effort.

Disordered breathing episodes may be classified as central disordered breathing, obstructive disordered breathing, or a combination of central and obstructive types. Various forms of disordered breathing that may be classified with respect to origin (central, obstructive, or mixed origin) may include, for example, apnea, hypopnea, hyperpnea, tachypnea, periodic breathing, Cheyne-Stokes respiration (CSR), and/or other forms of disordered breathing.

FIG. 1A is a flowchart of a method of classifying a disordered breathing event in accordance with embodiments of the invention. The method involves detecting 110 a disordered breathing event and sensing 120 motion associated with respiratory effort during the disordered breathing event. Disordered breathing may be detected based on the patient's respiration patterns, or by other methods. Motion associated with respiratory effort may be involve chest wall motion, abdominal motion and/or other motions associated with respiratory effort. The disordered breathing event may be classified 130 as central, obstructive, or a mixture of central and obstructive types based on the patient's movements associated with respiratory effort during the disordered breathing event.

In one scenario, the disordered breathing event may include both central and obstructive types. The disordered breathing event may be classified as a mixed central and obstructive disordered breathing event if central disordered breathing is classified during one portion of the disordered breathing event and obstructive disordered breathing is classified during another portion of the disordered breathing event.

Figure 1B:
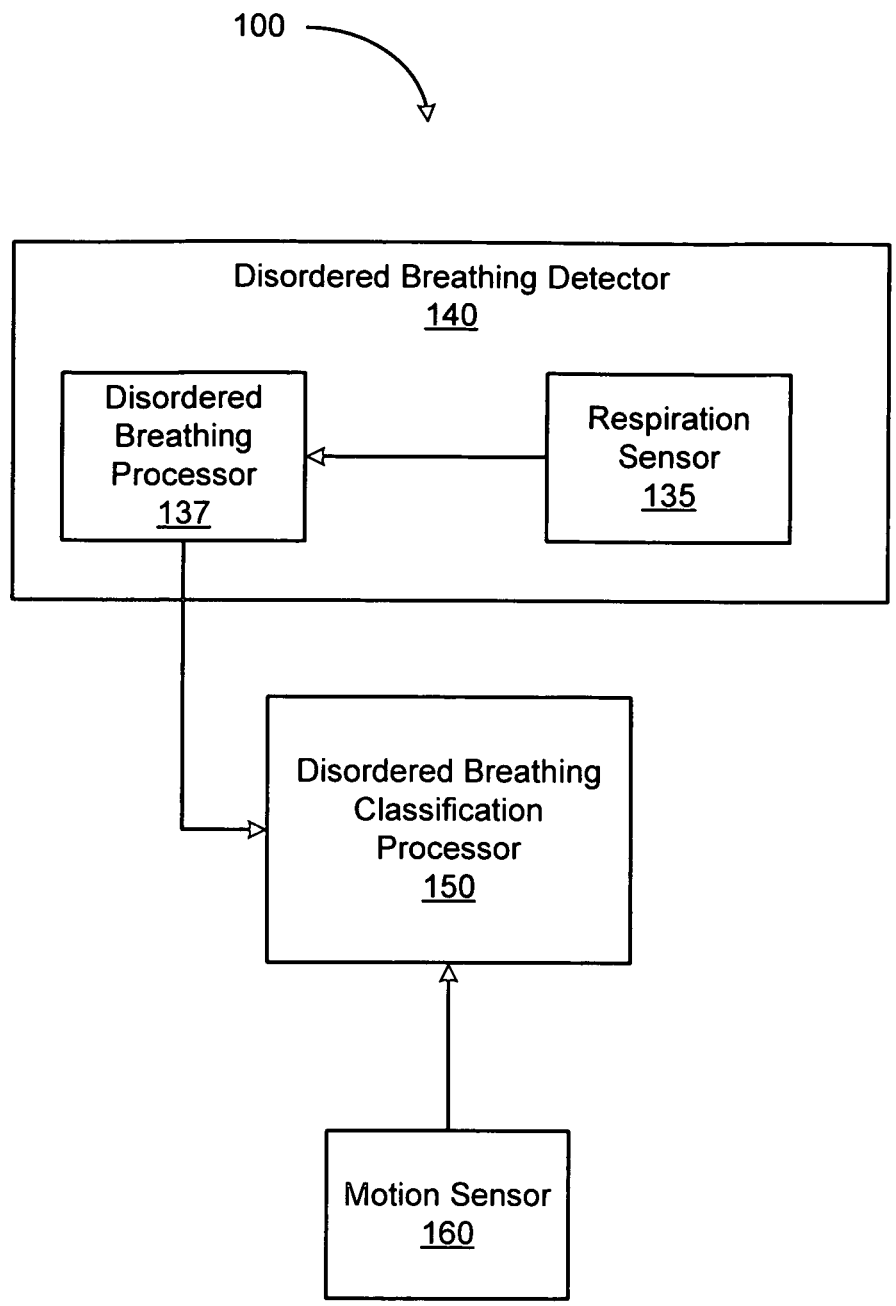
FIG. 1B is a block diagram of a disordered breathing classification system in accordance with embodiments of the invention.

FIG. 1B is a block diagram of a disordered breathing classification system 100 in accordance with embodiments of the invention. The disordered breathing classification system 100 illustrated in FIG. 1B includes a disordered breathing classification processor 150 that receives signals from a disordered breathing detector 140 and a motion sensor 160.

The disordered breathing detector 140 includes at least one sensor 135 for detecting a physiological signal indicative of disordered breathing. The sensor signals are communicated to the disordered breathing processor 137. The disordered breathing processor 137 analyzes the sensor signals and may determine that a disordered breathing event is in progress based on the analysis.

In one implementation, the sensor 135 generates a signal modulated by patient respiration. Such a signal may be generated, for example, by a transthoracic impedance sensor, an airflow meter, or by other sensing methods. A disordered breathing event may be detected based on the patient's breath intervals and/or tidal volume as described more fully below.

The motion sensor 160 may be configured to sense chest wall motion, abdominal motion, and/or other patient movement indicative of respiratory effort. The motion sensor 160 generates a signal indicative of respiratory effort that is communicated to the disordered breathing classification processor 150.

The sensors 135, 160 may comprise any number of patient-internal and/or patient-external sensors coupled through leads or wirelessly to other components of the disordered breathing classification system 100. In various embodiments, a signal indicative of the patient's respiration may be acquired using an implantable or patient-external transthoracic impedance sensor, blood oxygen sensor, microphone, flow meter, or by other patient-internal and/or patient-external sensing methods.

Sensing chest, abdominal, or other respiratory effort motion may be accomplished using a patient-internal or patient-external sensing device. In one example, patient motion associated with respiratory effort may be sensed using an implanted or patient-external accelerometer. The accelerometer may be incorporated as a component of an implanted medical device.

In another example, motion associated with respiratory effort may be detected based on changes in an electromyogram (EMG) sensor signal. An EMG sensor may be positioned internally or externally to detect electrical activity of a patient's intercostal, pectoral and/or diaphragmatic muscles indicative of motion, for example. In yet another example, motion associated with respiratory effort may be detected using a transthoracic impedance sensor. The patient's transthoracic impedance is modulated as the chest wall and/or abdomen moves during inspiratory attempts. Transthoracic impedance may be sensed using intracardiac electrodes, subcutaneous electrodes, or patient-external electrodes positioned at appropriate locations in, on, or about the patient's thorax for example.

A disordered breathing event may be classified as a central, obstructive or mixed type based on the based on the patient's respiratory efforts during disordered breathing episodes. The disordered breathing classification processor 150 may discriminate between central and obstructive disordered breathing events using signals received from the motion sensor 160 and the disordered breathing detector 140. If patient motion associated with respiratory effort is of sufficient magnitude during disordered breathing, then the disordered breathing classification processor 150 may determine that the disordered breathing event is obstructive in origin. If respiratory effort motion is insufficient during the disordered breathing event, then the disordered breathing classification processor 150 may be classify the disordered breathing event as central in origin. If the respiratory effort motion is sufficient during one portion of the disordered breathing episode, but is insufficient during another portion, then the disordered breathing classification processor 150 may classify the episode as a mixture of central and obstructive types.

In one configuration, the disordered breathing classification system 100 may be fully patient-external. In another configuration, some functions of the disordered breathing classification system may be implemented in an implantable device and other functions may be implemented as a patient external device. The implantable and the patient-external disordered breathing classification system components may be coupled through leads or a wireless communications link, such as through a Blue Tooth or a proprietary wireless communication link.

In yet another configuration, the disordered breathing classification system may be fully implantable. A fully implantable disordered breathing classification system may be incorporated, for example, as a component of a cardiac device such as a pacemaker, defibrillator, cardiac resynchronizer, implantable cardiac monitor, or other implantable medical device.

Figure 2:
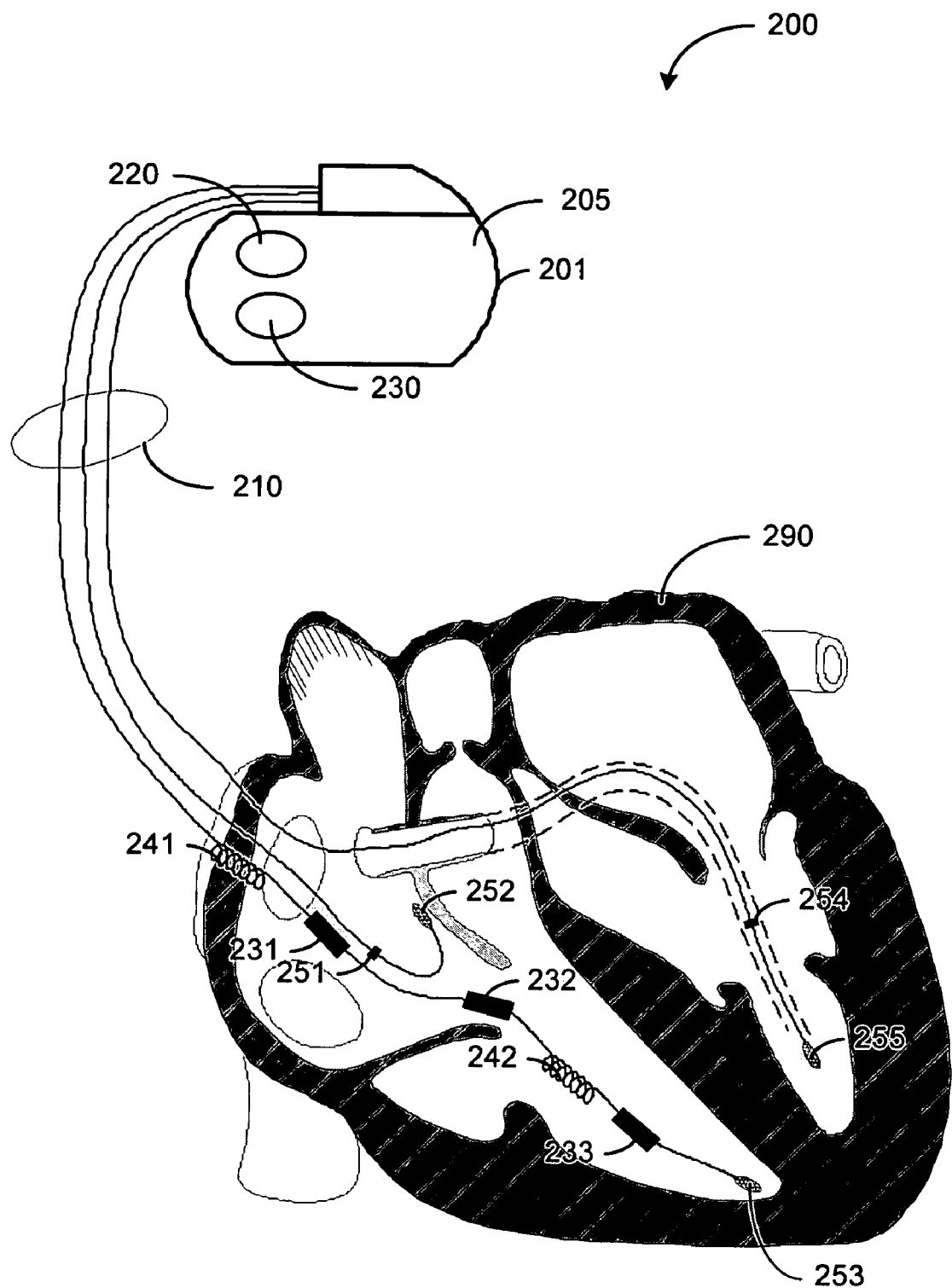
FIG. 2 is a partial view of an implantable device that may include a disordered breathing classification system in accordance with embodiments of the invention.

FIG. 2 is a partial view of an implantable device that may include a disordered breathing classification system in accordance with embodiments of the invention. The implantable device illustrated in FIG. 2 represents a cardiac rhythm management device (CRM) 200 that includes an implantable pulse generator 205 electrically and physically coupled to an intracardiac lead system 210. Portions of the intracardiac lead system 210 are inserted into the patient's heart 290. The intracardiac lead system 210 includes one or more electrodes configured to sense electrical cardiac activity of the heart, provide electrical stimulation to the heart, and/or to sense the patient's transthoracic impedance. Portions of the housing 201 of the pulse generator 205 may optionally serve as a can electrode.

Communications circuitry is disposed within the housing 201 for facilitating communication between the pulse generator 205 and an external communication device, such as a portable or bed-side communication station, patient-carried/worn communication station, or external programmer, for example. The communications circuitry can also facilitate unidirectional or bidirectional communication with one or more external, cutaneous, or subcutaneous physiologic or non-physiologic sensors, patient-input devices and/or information systems.

The pulse generator 205 may incorporate a motion detector 220 that may be used to sense the patient's chest wall movements associated with respiratory effort. The motion detector 220 may be implemented as an accelerometer positioned, for example, in or on the housing 201 of the pulse generator 205.

The lead system 210 of the CRM 200 may incorporate a transthoracic impedance sensor used to sense the patient's respiration. In one configuration, the transthoracic impedance sensor may include one or more intracardiac impedance electrodes. 231-233 positioned in one or more chambers of the heart 290 and impedance drive/sense circuitry 230 within the housing of the pulse generator 205.

The impedance drive/sense circuitry 230 generates a current that flows through the tissue between an impedance drive electrode 233 and a can electrode on the housing 201 of the pulse generator 205. The voltage at the impedance sense electrode 231, 232 relative to the can electrode changes as the patient's transthoracic impedance changes. The voltage signal developed between the impedance sense electrode 231, 232 and the can electrode is detected by the impedance drive/sense circuitry 230.

Figure 6:
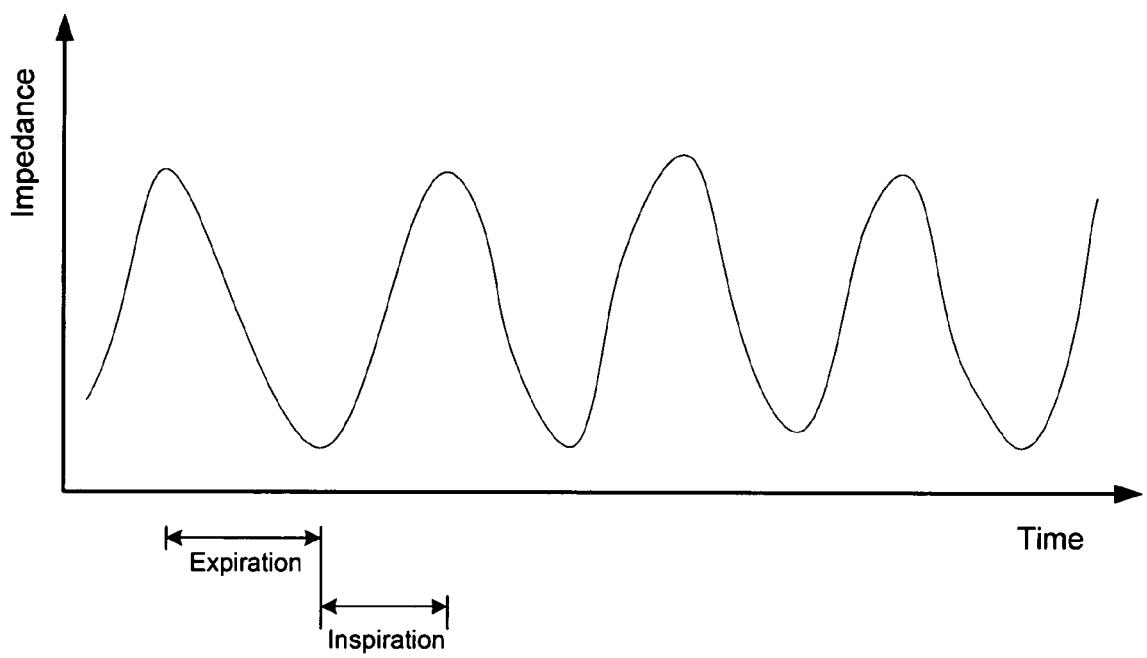
FIG. 6 is a graph of a respiration signal generated by a transthoracic impedance sensor that may be used in connection with classification of disordered breathing events in accordance with embodiments of the invention.

The voltage signal developed at the impedance sense electrode, 231, 232, illustrated in FIG. 6, is proportional to the patient's transthoracic impedance. Transthoracic impedance increases during respiratory inspiration and decreases during respiratory expiration. The peak-to-peak transition of the impedance, illustrated in FIG. 6, is proportional to the amount of air inhaled in one breath, denoted the tidal volume. The amount of air moved per minute is denoted the minute ventilation.

One or more pace/sense electrodes 251-255 may be positioned in one or more heart chambers for sensing electrical signals from the patient's heart 290 and/or delivering pacing pulses to the heart 290. The sense/pace electrodes 251-255 can be used to sense and pace one or more chambers of the heart, including the left ventricle, the right ventricle, the left atrium, and/or the right atrium. The lead system 210 may optionally include one or more defibrillation electrodes 241, 242 for delivering defibrillation/cardioversion shocks to the heart.

The pulse generator 205 may incorporate circuitry for detecting cardiac arrhythmias and circuitry for providing therapy in the form of electrical stimulation delivered to the heart through the lead system 210. A disordered breathing classification processor may also be incorporated within the pulse generator housing for classifying disordered breathing events in accordance with embodiments of the invention.

Figure 3:
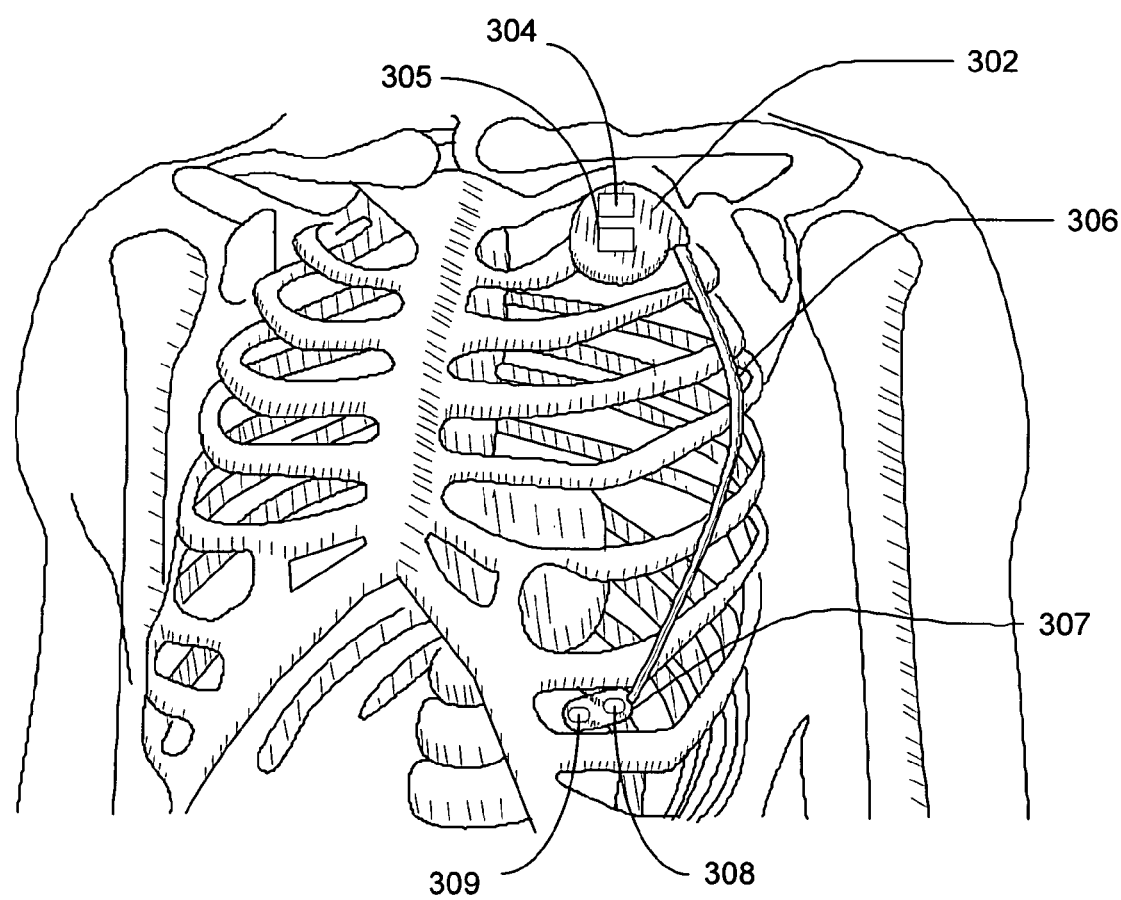
FIG. 3 is a diagram illustrating an implantable transthoracic cardiac device that may be used in connection with discrimination of central and obstructive disordered breathing in accordance with embodiments of the invention.

FIG. 3 is a diagram illustrating another configuration of an implantable medical device that may be used in connection with classification of disordered breathing in accordance with embodiments of the invention. The implantable device illustrated in FIG. 3 is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. Elements of the ITCS device may be located at several different body locations, such as in the chest, abdominal, or subclavian region with electrode elements respectively positioned at different regions near, around, in, or on the heart.

The ITCS device may incorporate a disordered breathing system for discriminating between types of disordered breathing. Portions of the classification system may be positioned within the primary housing 302 of the ITCS device. The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

Communications circuitry is disposed within the housing 302 for facilitating communication between the ITCS device and an external communication device, such as a portable or bed-side communication station, patient-carried/worn communication station, or external programmer, for example. The communications circuitry can also facilitate unidirectional or bidirectional communication with one or more external, cutaneous, or subcutaneous: physiologic or non-physiologic sensors. The housing 302 is typically configured to include one or more electrodes (e.g., can electrode and/or indifferent electrode).

In the configuration shown in FIG. 3, a subcutaneous electrode assembly 307 can be positioned under the skin in the chest region and situated distal from the housing 302. The subcutaneous and, if applicable, housing electrode(s) can be positioned about the heart at various locations and orientations, such as at various anterior and/or posterior locations relative to the heart. The subcutaneous electrode assembly 307 is coupled to circuitry within the housing 302 via a lead assembly 306. One or more conductors (e.g., coils or cables) are provided within the lead assembly 306 and electrically couple the subcutaneous electrode assembly 307 with circuitry in the housing 302. One or more chest wall motion sensors and/or transthoracic impedance electrodes along with one or more cardiac sense, sense/pace or defibrillation electrodes can be situated on the elongated structure of the lead assembly 306, the housing 302, and/or the distal electrode assembly (shown as subcutaneous electrode assembly 307 in the configuration shown in FIG. 3).

In particular configurations, the ITCS device may perform functions traditionally performed by cardiac rhythm management devices, such as providing various cardiac monitoring, pacing and/or cardioversion/defibrillation functions. Exemplary pacemaker circuitry, structures and functionality, aspects of which can be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations can provide for non-physiologic pacing support in addition to, or to the exclusion of, bradycardia and/or anti-tachycardia pacing therapies. Exemplary cardiac monitoring circuitry, structures and functionality, aspects of which can be incorporated in an ITCS of the present invention, are disclosed in commonly owned U.S. Pat. Nos. 5,313,953; 5,388,578; and 5,411,031, which are hereby incorporated herein by reference in their respective entireties.

An ITCS device can incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243 and commonly owned U.S. patent applications "Subcutaneous Cardiac Sensing, Stimulation, Lead Delivery, and Electrode Fixation Systems and Methods," Ser. No. 60/462,272, filed Apr. 11, 2003, and U.S. Publication Nos. 2004/0230229 and 2004/0230230, which are incorporated by reference.

In FIG. 3, there is shown a configuration of a transthoracic cardiac sensing and/or stimulation (ITCS) device incorporating a disordered breathing classification system having components implanted in the chest region of a patient at different locations. The disordered breathing classification system may be used to discriminate between central and obstructive disordered breathing events and/or to classify disordered breathing events in accordance with embodiments of the invention. In the particular configuration shown in FIG. 3, the ITCS device includes a primary housing 302, lead assembly 306, and a subcutaneous electrode assembly 307. Various sensing, detection, processing, and energy delivery circuitry for disordered breathing classification and/or discrimination can be positioned within, on, and/or about the components of the ITCS. For example, a disordered breathing classification processor 304, a patient motion sensor 305, and/or portions of a disordered breathing detector may be positioned on or within the primary housing 302, the lead assembly 306, and/or the subcutaneous electrode assembly 307 of the ITCS device.

In one embodiment, a disordered breathing classification processor 304 is located within the primary housing 302 of the ITCS. The patient motion sensor 305 comprises an accelerometer positioned in or on the primary housing 302 of the ITCS. The accelerometer is configured to sense patient motion associated with respiratory effort. In this embodiment, a transthoracic impedance sensor is used to sense patient respiration. The transthoracic impedance sensor may include impedance drive/sense circuitry within the housing 302 coupled to a can electrode and to one or more impedance electrodes 308, 309 positioned on the subcutaneous electrode assembly 307. The impedance drive circuitry generates a current that flows between a subcutaneous impedance drive electrode 309 and the can electrode on the primary housing 302 of the ITCS device. The voltage at a subcutaneous impedance sense electrode 308 relative to the can electrode changes as the patient's transthoracic impedance changes. The voltage signal developed between the impedance sense electrode 308 and the can electrode is sensed by the impedance sense circuitry, producing a signal such as that depicted in FIG. 6.

As previously discussed, the transthoracic impedance signal is related to patient respiration, with impedance increasing during respiratory inspiration and decreasing with respiratory expiration. Respiration signals generated by the transthoracic impedance sensor may be used to by the disordered breathing detector to detect disordered breathing. Respiration signals may be used in conjunction with patient motion signals associated with respiratory effort for classification and/or discrimination of the origin of disordered breathing events.

Figure 4:
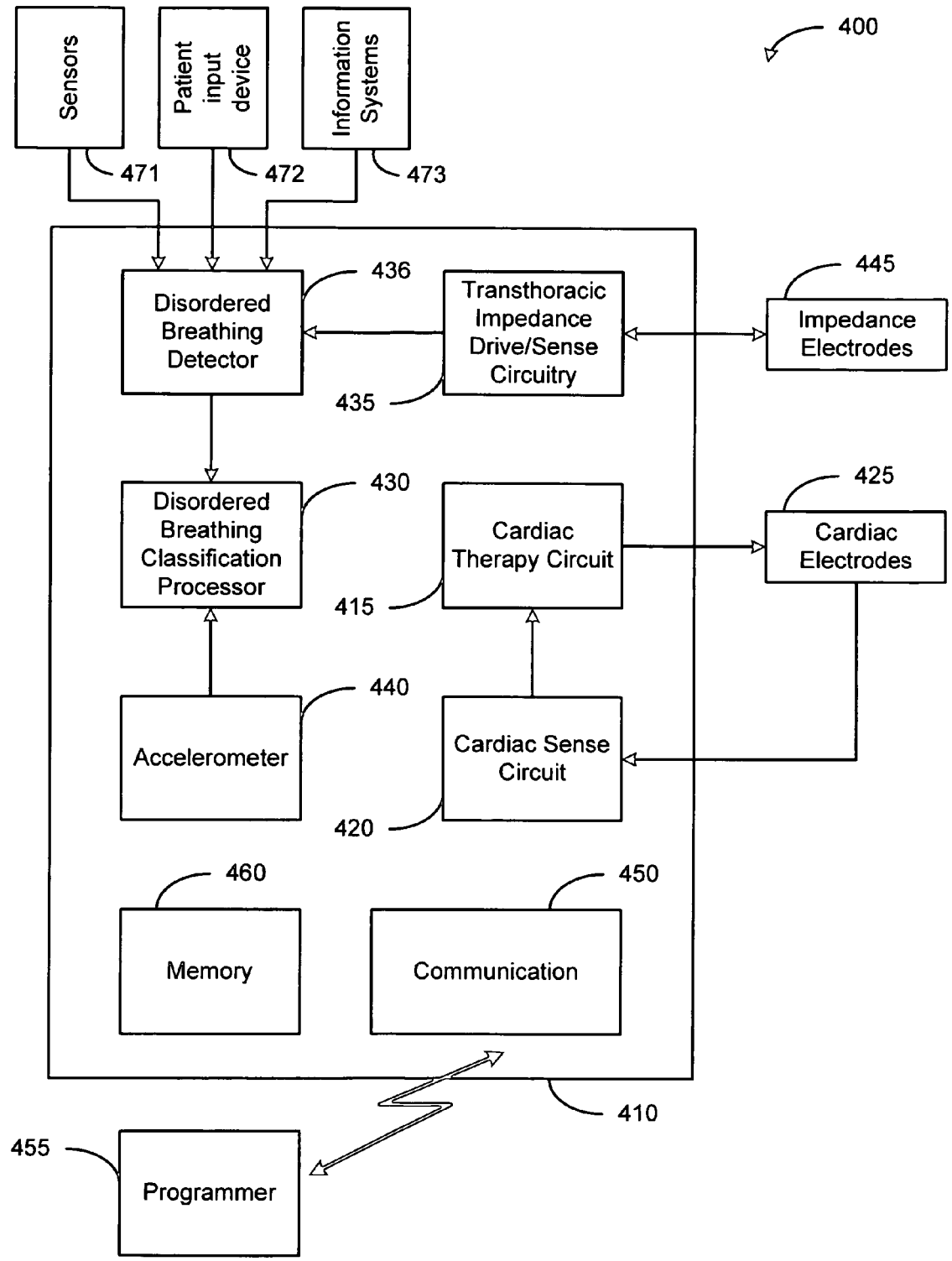
FIG. 4 is a block diagram of an implantable medical system including a disordered breathing classification system in accordance with embodiments of the invention.

FIG. 4 is a block diagram of an implantable medical system 400 comprising an implantable cardiac device 410 incorporating a disordered breathing classification system in accordance with embodiments of the invention. The cardiac device 410 includes a cardiac therapy circuit 415 and a cardiac sense circuit 420 coupled through a lead system to cardiac electrodes 425. The cardiac electrodes 425 are electrically coupled to the patient's heart for sensing electrical cardiac signals and/or delivering therapy to the heart in the form of electrical stimulation energy, e.g., pacing pulses and/or defibrillation/cardioversion shocks.

The cardiac device 410 illustrated in FIG. 4 includes a disordered breathing classification processor 430 coupled to an accelerometer 440 and to a disordered breathing detector 436. The accelerometer 440 senses patient motion associated with respiratory effort, e.g., motion of the chest wall, abdomen diaphragm, and/or thorax and generates a signal corresponding to patient movement associated with respiratory effort. Transthoracic impedance drive/sense circuitry 435 and transthoracic impedance electrodes 445 together form a transthoracic impedance sensor capable of producing a signal representative of the patient's respiration. The disordered breathing detector 436 may detect disordered breathing episodes based on the patient's respiration patterns, or by other methods. The disordered breathing classification processor 430 classifies the disordered breathing events as central, obstructive or mixed disordered breathing events based on signals received from the accelerometer 440 and the disordered breathing detector 436.

Various conditions affecting the patient that may be used for disordered breathing detection can be acquired using patient-internal or patient-external sensors 471, patient input devices 472 and/or other information systems 473. The one or more of the conditions sensed using the sensors 471, patient input device 472, and/or other information systems 473 may be used in addition to the transthoracic impedance signal or in place of the transthoracic impedance signal for disordered breathing detection as described more fully below.

The sensors 471 may comprise patient-internal and/or patient-external sensors coupled through leads or wirelessly to the implantable device 410. The patient input device 472 allows the patient to input information relevant to disordered breathing detection. For example, the patient input device 472 may be particularly useful for inputting information concerning patient-known information relevant to disordered breathing detection, such as information related to patient sleep times, smoking, drug use, and/or patient perceptions that are not automatically sensed or detected by the medical device 410.

The medical device 410 may also be coupled to one or more information systems 473, such as network-connected servers. The implantable device 410, may access the information systems 473 to acquire information about conditions associated with an increased or decreased incidence of disordered breathing in the patient. For example, the implantable device 410 may access an air quality website to acquire information about the ambient pollution index that may be used in disordered breathing detection.

The medical device 410 includes a memory circuit 460 that may be used to store data and/or programming commands. For example, the memory circuit 460 may be used to store information related to disordered breathing, such as information about the occurrence of one or more disordered breathing events, the classified origin of one or more disordered breathing events, and/or conditions or thresholds used for disordered breathing detection. Stored information maybe wirelessly transmitted to a remote device 455, such as a device programmer and/or a patient management server. The communications circuitry 450 of the implantable device 410 may be used to implement wireless communication with the remote device 455 through a wireless communication link, e.g., Bluetooth or proprietary wireless link. Further, the communications circuitry 450 may be used to couple the medical device 410 to one or more internal, external, cutaneous, subcutaneous physiologic or non-physiologic sensors, patient input devices and/or information systems.

Embodiments described herein may be used within the context of an advanced patient management system. Advanced patient management systems involve a system of medical devices that are accessible through various communications technologies. For example, patient data may be downloaded from one or more of the medical devices periodically or on command, and stored at a patient information server. The physician and/or the patient may communicate with the medical devices and the patient information server, for example, to submit or acquire patient data or to initiate, terminate or modify therapy.

Methods, structures, or techniques described herein relating to advanced patient management, such as remote patient monitoring, diagnosis, and/or therapy, or other advanced patient management methodologies can incorporate features of one or more of the following references: U.S. Pat. Nos. 6,221,011, 6,270,457, 6,280,380, 6,312,378, 6,336,903, 6,358,203, 6,368,284, 6,398,728, and 6,440,066 which are incorporated by reference.

Disordered breathing may be more effectively classified using a coordinated approach. Various embodiments of the invention are implemented using medical systems employing one or a number of patient-external and/or patient-internal medical devices. The medical devices may communicate or otherwise operate in concert to provide more comprehensive patient monitoring, diagnosis, and/or therapy for disordered breathing or other medical dysfunctions.

Figure 5:
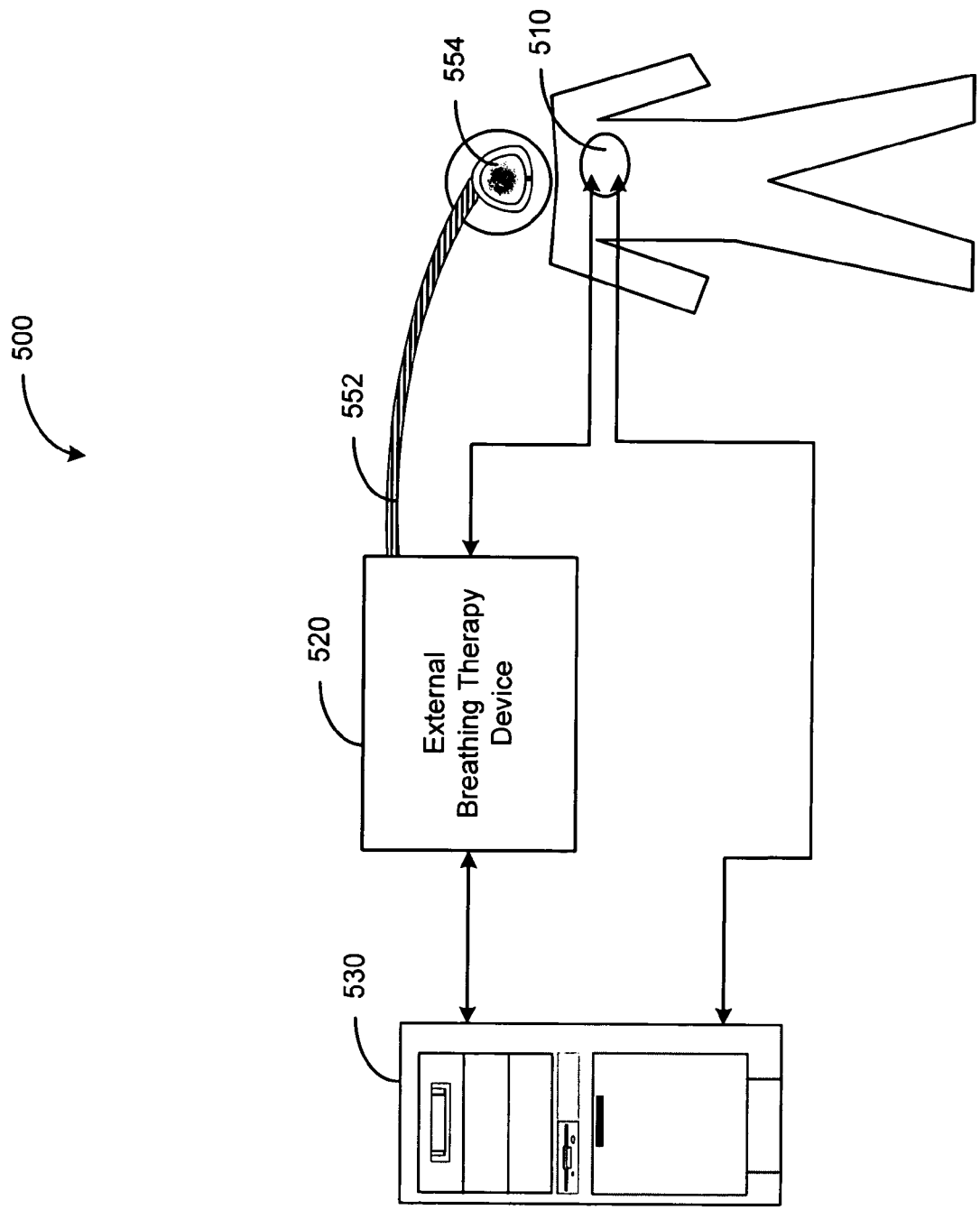
FIG. 5 is a block diagram illustrating a medical system including a patient-internal device that cooperates with a patient-external device to implement disordered breathing classification in accordance with embodiments of the invention.

The block diagram of FIG. 5 illustrates a medical system 500 including a patient-internal device 510 that cooperates with a patient-external device 520 to implement disordered breathing classification in accordance with embodiments of the invention. The patient-internal device 510 may comprise, for example, an implantable cardiac rhythm management system (CRM) such as a pacemaker, defibrillator, cardiac resynchronizer, or the like.

The patient-external device 520 may comprise, for example, an external breathing therapy device such as a continuous positive airway pressure device (CPAP), bi-level positive airway pressure device (bi-PAP) or other positive airway pressure device, generically referred to herein as xPAP devices. An xPAP device 520 develops a positive air pressure that is delivered to the patient's airway through tubing 552 and mask 554 connected to the xPAP device 520. Positive airway pressure devices are often used to treat disordered breathing. In one configuration, for example, the positive airway pressure provided by the xPAP device 520 acts as a pneumatic splint keeping the patient's airway open and reducing the severity and/or number of occurrences of disordered breathing events due to airway obstruction. In addition to delivering breathing therapy, sensors associated with the xPAP device 520, located on the xPAP mask or elsewhere, may provide information useful to a number of monitoring and/or diagnostic functions. For example, the xPAP device 520 may sense respiration using an oxygen sensor, a microphone, a flow meter, and/or other respiration sensing methods.

A disordered breathing detector and/or a disordered breathing classification processor may be incorporated in either the patient-internal CRM 510 device, the patient-external xPAP 520 device, or a remote computing device such as a patient management server 530. The CRM 510 may provide a first set of monitoring, diagnostic, and/or therapeutic functions to the patient. The xPAP device 520 may provide a second set of monitoring, diagnostic, and/or therapeutic functions to the patient. The CRM device 510, the xPAP device 520, or both may include sensors for sensing patient movement and/or respiration used for disordered breathing classification.

In one embodiment, the CRM device 510 may sense both respiration and patient movement associated with respiratory-effort. The sensed information may be transmitted to the xPAP device 520. Classification of disordered breathing events as to central, obstructive, or mixed origin may be implemented in the xPAP device based on the patient movement and respiration information transmitted from the CRM device 510.

In another embodiment, the CRM device 510 may sense patient movement associated with respiratory effort and the CPAP device 510 may sense patient respiration. Patient respiration information may be transmitted from the CPAP 520 device to the CRM device 510. The respiration information may be used by the CRM device 510 along with the patient movement information for classifying the disordered breathing events.

In yet another embodiment, CRM device 510 may sense patient movement and the CPAP device 510 may sense patient respiration. Patient respiration information may be transmitted from the CPAP 520 device and the CRM device 510 to a remote patient management server 530. The respiration and patient movement information may be used by the patient management server 530 for classifying disordered breathing events.

The processes described herein involve detecting a disordered breathing event and evaluating movements indicative of respiratory effort that occur during the disordered breathing event. A disordered breathing event may be detected by sensing and analyzing various conditions affecting the patient and associated with disordered breathing. Table 1 provides a representative set of patient conditions that may be used in connection with disordered breathing detection in accordance with embodiments of the invention. Table 1 also provides illustrative sensing methods that may be employed to sense the conditions.

Conditions used for disordered breathing detection may include both physiological and non-physiological contextual conditions affecting the patient. Physiological conditions may include a broad category of conditions associated with the internal functioning of the patient's physiological systems, including the cardiovascular, respiratory, nervous, muscle, and other body systems. Examples of physiological conditions that may be useful in the detection of disordered breathing include blood chemistry, patient posture, patient activity, respiration patterns, among others.

Contextual conditions are non-physiological conditions representing patient-external or background conditions. Contextual conditions may be broadly defined to include present environmental conditions, such as patient location, ambient temperature, humidity, air pollution index. Contextual conditions may also include historical/background conditions relating to the patient, including the patient's normal sleep time and the patient's medical history, for example. Methods and systems for detecting some contextual conditions, including, for example, proximity to bed detection, are described in commonly owned U.S. Patent 7,400,928, which is incorporated by reference herein in its entirety.

TABLE 1

| Condition Type | | Condition | Sensor type or Detection method |
|---|---|---|---|
| Physiological | Cardiovascular System | Heart rate | EGM, ECG |
| | | Heart rate variability | |
| | | QT interval | |
| | | Ventricular filling pressure | Intracardiac pressure sensor |
| | | Blood pressure | Blood pressure sensor |
| | Respiratory System | Snoring | Accelerometer |
| | | | Microphone |
| | | Respiration pattern (Tidal volume Minute ventilation Respiratory rate) | Transthoracic impedance sensor (AC) |
| | | Patency of upper airway | Intrathoracic impedance sensor |
| | | Pulmonary congestion | Transthoracic impedance sensor (DC) |
| | Nervous System | Sympathetic nerve activity | Muscle sympathetic nerve Activity sensor |
| | | Brain activity | EEG |
| | Blood Chemistry | $CO_2$ saturation | Blood analysis |
| | | $O_2$ saturation | |
| | | Blood alcohol content | |
| | | Adrenalin | |
| | | Brain Natriuretic Peptide (BNP) | |
| | | C-Reactive Protein | |
| | | Drug/Medication/Tobacco use | |

TABLE 1-continued

| Condition Type | | Condition | Sensor type or Detection method |
|---|---|---|---|
| | Muscle System | Muscle atonia | EMG |
| | | Eye movement | EOG |
| | | Patient activity | Accelerometer, MV, etc. |
| | | Limb movements | Accelerometer, EMG |
| | | Jaw movements | Accelerometer, EMG |
| | | Posture | Multi-axis accelerometer |
| Contextual | Environmental | Ambient temperature | Thermometer |
| | | Humidity | Hygrometer |
| | | Pollution | Air quality website |
| | | Time | Clock |
| | | Barometric pressure | Barometer |
| | | Ambient noise | Microphone |
| | | Ambient light | Photodetector |
| | | Altitude | Altimeter |
| | | Location | GPS, proximity sensor |
| | | Proximity to bed | Proximity to bed sensor |
| | Historical/Background | Historical sleep time | Patient input, previously detected sleep onset times |
| | | Medical history | Patient input |
| | | Age | |
| | | Recent exercise | |
| | | Weight | |
| | | Gender | |
| | | Body mass index | |
| | | Neck size | |
| | | Emotional state | |
| | | Psychological history | |
| | | Daytime sleepiness | |
| | | Patient perception of sleep quality | |
| | | Drug, alcohol, nicotine use | |

Table 2 provides examples of how a representative subset of the physiological and contextual conditions listed in Table 1 may be used in connection with disordered breathing detection.

It will be appreciated that patient conditions and detection methods other than those listed in Tables 1 and 2 may be used for disordered breathing detection and are considered to be within the scope of the invention.

TABLE 2

| Condition Type | Condition | Examples of how condition may be used in disordered breathing detection |
|---|---|---|
| Physiological | Heart rate | Decrease in heart rate may indicate disordered breathing episode. Increase in heart rate may indicate autonomic arousal from a disordered breathing episode. Decrease in heart rate may indicate the patient is asleep. |
| | Heart rate variability | Disordered breathing causes heart rate variability to decrease. Changes in HRV associated with sleep disordered breathing may be observed while the patient is awake or asleep |
| | Ventricular filling pressure | May be used to identify/predict pulmonary congestion associated with respiratory disturbance. |
| | Blood pressure | Swings in on-line blood pressure measures are associated with apnea. Disordered breathing generally increases blood pressure variability - these changes may be observed while the patient is awake or asleep. |
| | Snoring | Snoring is associated with a higher incidence of obstructive sleep apnea and may be used to detect disordered breathing. |
| | Respiration pattern/rate | Respiration patterns including, e.g., respiration rate, may be used to detect disordered breathing episodes. Respiration patterns may be used to determine the type of disordered breathing. Respiration patterns may be used to detect that the patient is asleep. |
| | Patency of upper airway | Patency of upper airway is related to obstructive sleep apnea and may be used to detect episodes of obstructive sleep apnea. |
| | Pulmonary congestion | Pulmonary congestion is associated with respiratory disturbances. |

TABLE 2-continued

| Condition Type | Condition | Examples of how condition may be used in disordered breathing detection |
|---|---|---|
| | Sympathetic nerve activity | End of apnea associated with a spike in SNA. Changes in SNA observed while the patient is awake or asleep may be associated with sleep disordered breathing |
| | $CO_2$ | Low $CO_2$ levels initiate central apnea. |
| | $O_2$ | $O_2$ desaturation occurs during severe apnea/hypopnea episodes. |
| | Blood alcohol content | Alcohol tends to increase incidence of snoring & obstructive apnea. |
| | Adrenalin | End of apnea associated with a spike in blood adrenaline. |
| | BNP | A marker of heart failure status, which is associated with Cheyne-Stokes Respiration |
| | C-Reactive Protein | A measure of inflammation that may be related to apnea. |
| | Drug/Medication/Tobacco use | These substances may affect the incidence of both central & obstructive apnea. |
| | Muscle atonia | Muscle atonia may be used to detect REM and non-REM sleep. |
| | Eye movement | Eye movement may be used to detect REM and non-REM sleep. |
| Contextual | Temperature | Ambient temperature may be a condition predisposing the patient to episodes of disordered breathing and may be useful in disordered breathing detection. |
| | Humidity | Humidity may be a condition predisposing the patient to episodes of disordered breathing and may be useful in disordered breathing detection. |
| | Pollution | Pollution may be a condition predisposing the patient to episodes of disordered breathing and may be useful in disordered breathing detection. |
| | Posture | Posture may be used to confirm or determine the patient is asleep. |
| | Activity | Patient activity may be used in relation to sleep detection. |
| | Location | Patient location may used to determine if the patient is in bed as a part of sleep detection. |
| | Altitude | Lower oxygen concentrations at higher altitudes tends to cause more central apnea |

Detection of disordered breathing may involve comparing one condition or multiple conditions to one or more thresholds or other indices indicative of disordered breathing. A threshold or other index indicative of disordered breathing may comprise a predetermined level of a particular condition, e.g., blood oxygen level less than a predetermined amount. A threshold or other index indicative of disordered breathing may comprises a change in a level of a particular condition, e.g., heart rate decreasing from a sleep rate to lower rate within a predetermined time interval.

In one approach, the relationships between the conditions may be indicative of disordered breathing. In this approach, disordered breathing detection may be based on the existence and relative values associated with two or more conditions. For example, if condition A is present at a level of x, then condition B must also be present at a level of f(x) before a disordered breathing detection is made.

The thresholds and/or relationships indicative of disordered breathing may be highly patient specific. The thresholds and/or relationships indicative of disordered breathing may be determined on a case-by-case basis by monitoring the conditions and monitoring disordered breathing episodes. The analysis may involve determining levels of the monitored conditions and/or relationships between the monitored conditions associated, e.g., statistically correlated, with disordered breathing episodes. The thresholds and/or relationships used in disordered breathing detection may be updated periodically to track changes in the patient's response to disordered breathing.

In various implementations, episodes of disordered breathing may be detected through analysis of the patient's respiration patterns. Methods and systems of disordered breathing detection based on respiration patterns are further described in commonly owned U.S. Pat. No. 7,252,640, which is incorporated by reference.

FIG. 6 illustrates normal respiration signal generated by a transthoracic impedance sensor. Transthoracic impedance increases during respiratory inspiration and decreases during respiratory expiration. A normal "at rest" respiration pattern, e.g., during non-REM sleep, includes regular, rhythmic inspiration-expiration cycles without substantial interruptions.

In various embodiments, episodes of disordered breathing may be detected by monitoring the respiratory waveform signal generated by a transthoracic impedance sensor. In one example, when the tidal volume (TV) of the patient's respiration, as indicated by the transthoracic impedance signal, falls below a hypopnea threshold, then a hypopnea event is declared. A hypopnea event may be declared, for example, if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

Figure 7:
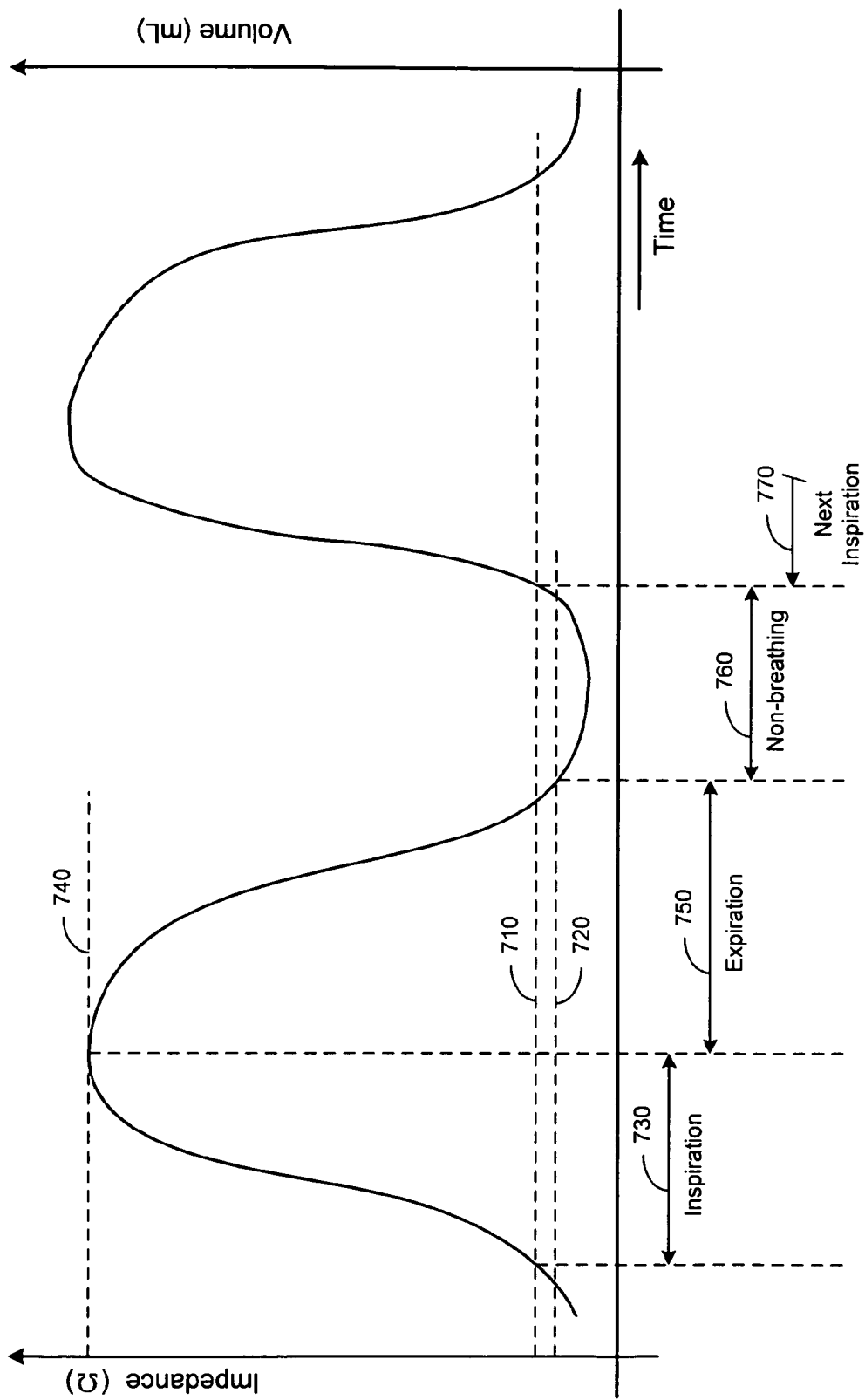
FIG. 7 is a graph illustrating respiration intervals used for disordered breathing detection according to embodiments of the invention.

In another embodiment, detection of disordered breathing involves defining and analyzing respiratory cycle intervals. FIG. 7 is a graph illustrating respiration intervals used for disordered breathing detection according to embodiments of the invention. A respiration cycle is divided into an inspiration period 730 corresponding to the patient inhaling, an expiration period 750, corresponding to the patient exhaling, and a non-breathing period 760 occurring between inspiration 730 and expiration 750. Respiration intervals are established using inspiration 710 and expiration 720 thresholds. The inspiration threshold 710 marks the beginning of an inspiration period 730 and is determined by the transthoracic impedance signal rising above the inspiration threshold 710. The inspiration period 730 ends when the transthoracic impedance signal is maximum 740. A maximum transthoracic impedance signal 740 corresponds to both the end of the inspiration interval 730 and the beginning of the expiration interval 750. The expiration interval 750 continues until the transthoracic impedance falls below an expiration threshold 720. A non-breathing interval 760 starts from the end of the expiration period 750 and continues until the beginning of the next inspiration period 770.

Figure 8:
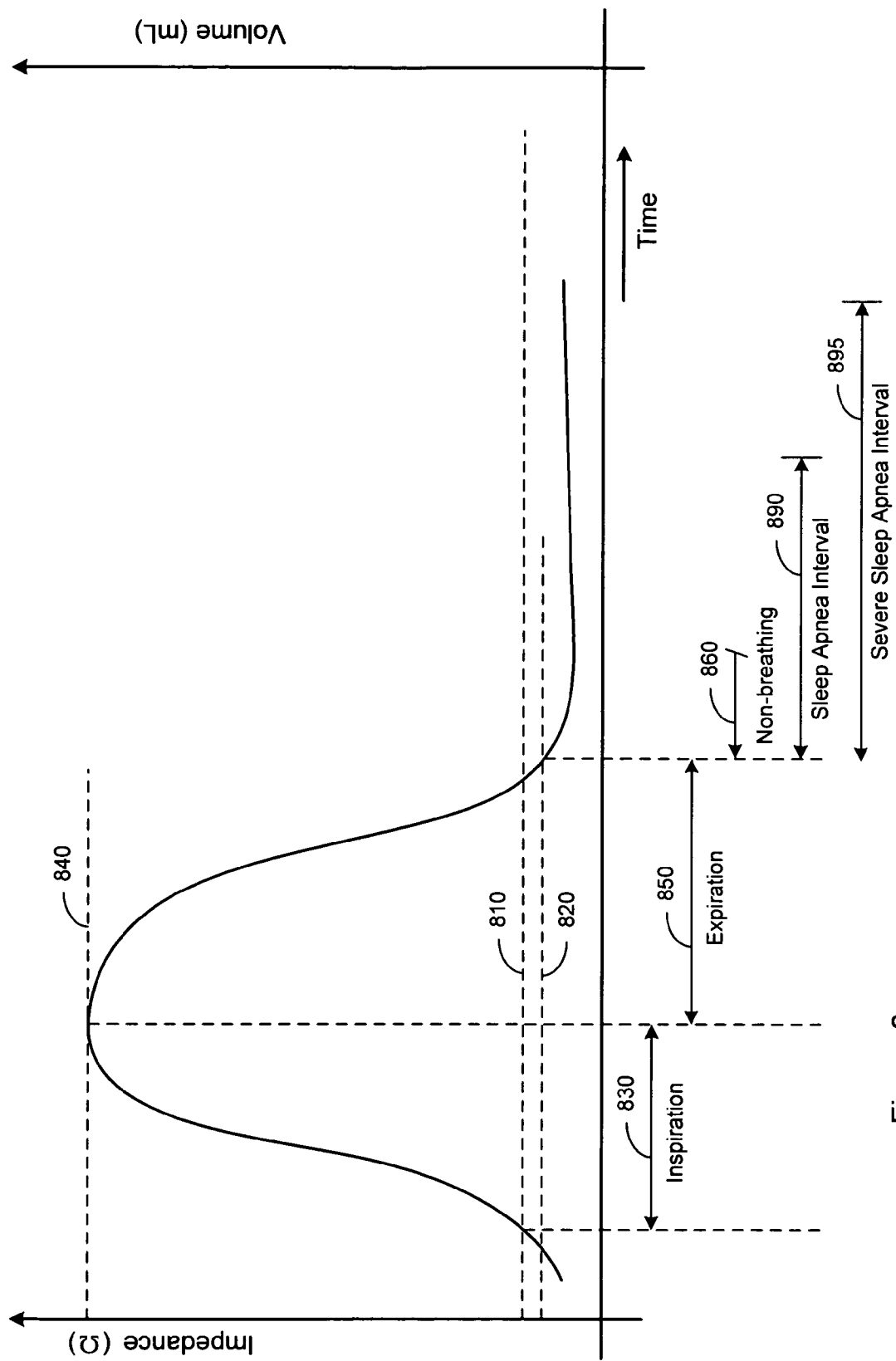
FIG. 8 is a graph illustrating detection of sleep apnea and severe sleep apnea in accordance with embodiments of the invention.

Detection of sleep apnea and/or severe sleep apnea according to embodiments of the invention is illustrated in FIG. 8. The patient's respiration signals are monitored and the respiration cycles are defined according to inspiration 830, expiration 850, and non-breathing 860 intervals as described in connection with FIG. 7. A condition of sleep apnea is detected when a non-breathing period 860 exceeds a first predetermined interval 890, denoted the sleep apnea interval. A condition of severe sleep apnea is detected when the non-breathing period 860 exceeds a second predetermined interval 895, denoted the severe sleep apnea interval. For example, sleep apnea may be detected when the non-breathing interval exceeds about 10 seconds, and severe sleep apnea may be detected when the non-breathing interval exceeds about 20 seconds.

Figure 9A:
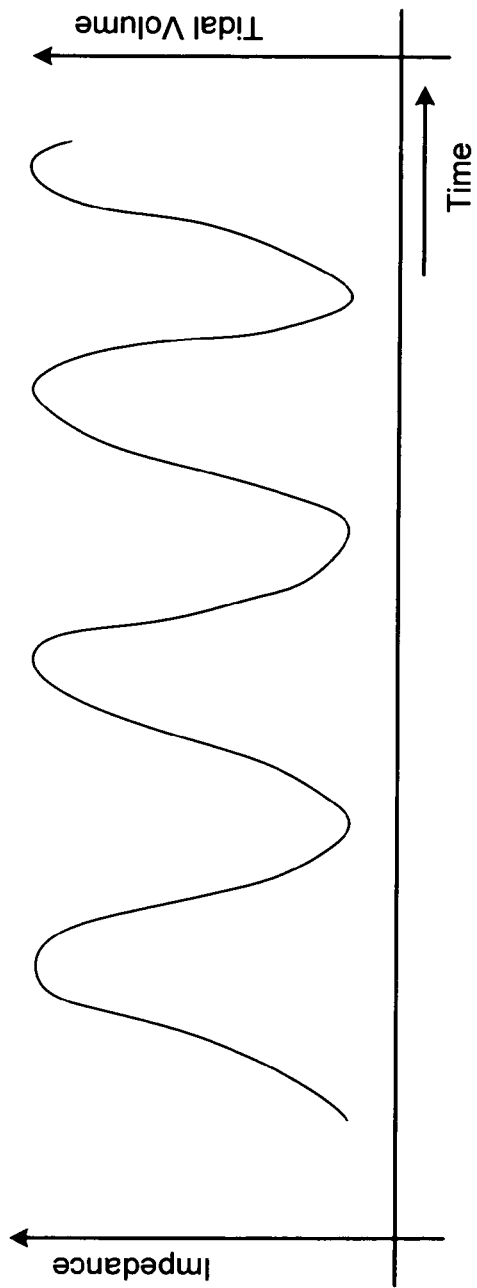
FIGS. 9A and 9B illustrate respiration patterns associated with normal respiration and abnormally shallow respiration, respectively, utilized in accordance with embodiments of the invention.
Figure 9B:
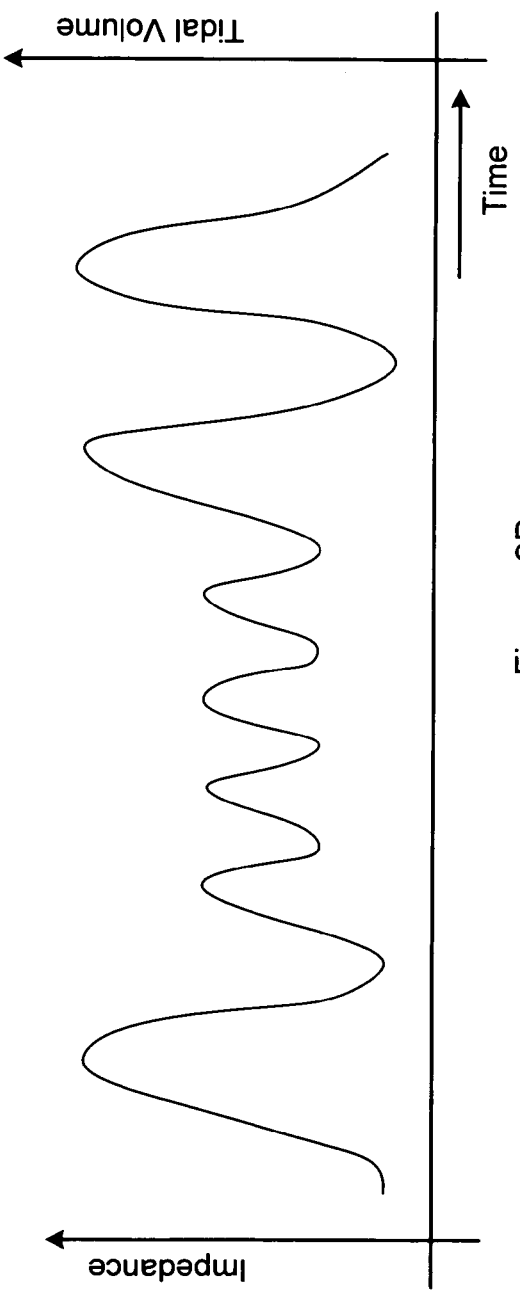

Hypopnea is a condition of disordered breathing characterized by abnormally shallow breathing. FIGS. 9A-9B are graphs of tidal volume derived from transthoracic impedance measurements. The graphs compare the tidal volume of a normal breathing cycle to the tidal volume of a hypopnea episode. FIG. 9A illustrates normal respiration tidal volume and rate. As shown in FIG. 9B, hypopnea involves a period of abnormally shallow respiration.

According to an embodiment of the invention, hypopnea may be detected by comparing a patient's respiratory tidal volume to a hypopnea tidal volume threshold. The tidal volume for each respiration cycle is derived from transthoracic impedance measurements acquired in the manner described above. The hypopnea tidal volume threshold may be established using clinical results providing a representative tidal volume and duration of hypopnea events. In one configuration, hypopnea is detected when an average of the patient's respiratory tidal volume taken over a selected time interval falls below the hypopnea tidal volume threshold. Furthermore, various combinations of hypopnea cycles, breath intervals, and non-breathing intervals may be used to detect hypopnea, where the non-breathing intervals are determined as described above.

Figure 10:
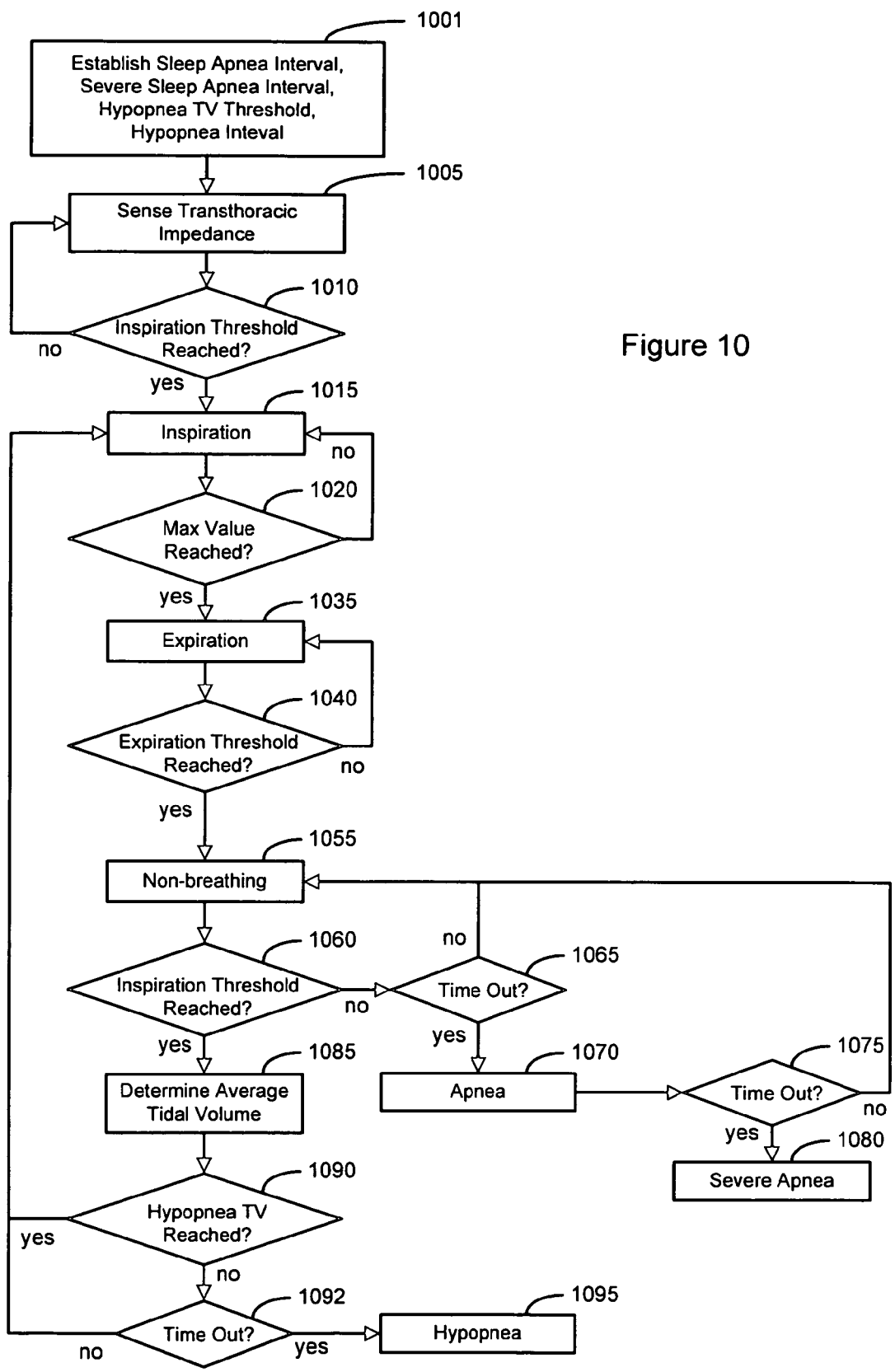
FIG. 10 is a flow chart illustrating a method of apnea and/or hypopnea detection according to embodiments of the invention.

FIG. 10 is a flow chart illustrating a method of apnea and/or hypopnea detection according to embodiments of the invention. Various parameters are established 1001 before analyzing the patient's respiration for disordered breathing episodes, including, for example, inspiration and expiration thresholds, sleep apnea interval, severe sleep apnea interval, and hypopnea tidal volume threshold.

The patient's transthoracic impedance is determined 1005 as described in more detail above. If the transthoracic impedance exceeds 1010 the inspiration threshold, the beginning of an inspiration interval is detected 1015. If the transthoracic impedance remains below 1010 the inspiration threshold, then the impedance signal is checked 1005 periodically until inspiration 1015 occurs.

During the inspiration interval, the patient's transthoracic impedance is monitored until a maximum value of the transthoracic impedance is detected 1020. Detection of the maximum value signals an end of the inspiration period and a beginning of an expiration period 1035.

The expiration interval is characterized by decreasing transthoracic impedance. When the transthoracic impedance falls 1040 below the expiration threshold, a non-breathing interval is detected 1055.

If the transthoracic impedance does not exceed 1060 the inspiration threshold within a first predetermined interval 1065, denoted the sleep apnea interval, then a condition of sleep apnea is detected 1070. Severe sleep apnea is detected 1080 if the non-breathing period extends beyond a second predetermined interval 1075, denoted the severe sleep apnea interval.

When the transthoracic impedance exceeds 1060 the inspiration threshold, the tidal volume from the peak-to-peak transthoracic impedance is calculated, along with a moving average of past tidal volumes 1085. The peak-to-peak transthoracic impedance provides a value proportional to the tidal volume of the respiration cycle. This value is compared to a hypopnea tidal volume threshold 1090. If the peak-to-peak transthoracic impedance is consistent with the hypopnea tidal volume threshold 1090 for a predetermined time 1092, then a hypopnea cycle is detected 1095.

Additional sensors, such as motion sensors and/or posture sensors, may be used to confirm or verify the detection of a sleep apnea or hypopnea episode. The additional sensors may be employed to prevent false or missed detections of sleep apnea/hypopnea due to posture and/or motion related artifacts.

Another embodiment of the invention involves classifying respiration patterns as disordered breathing episodes based on the breath intervals and/or tidal volumes of one or more respiration cycles within the respiration patterns. According to this embodiment, the duration and tidal volumes associated with a respiration pattern are compared to duration and tidal volume thresholds. The respiration pattern is detected as a disordered breathing episode based on the comparison.

Figure 11:
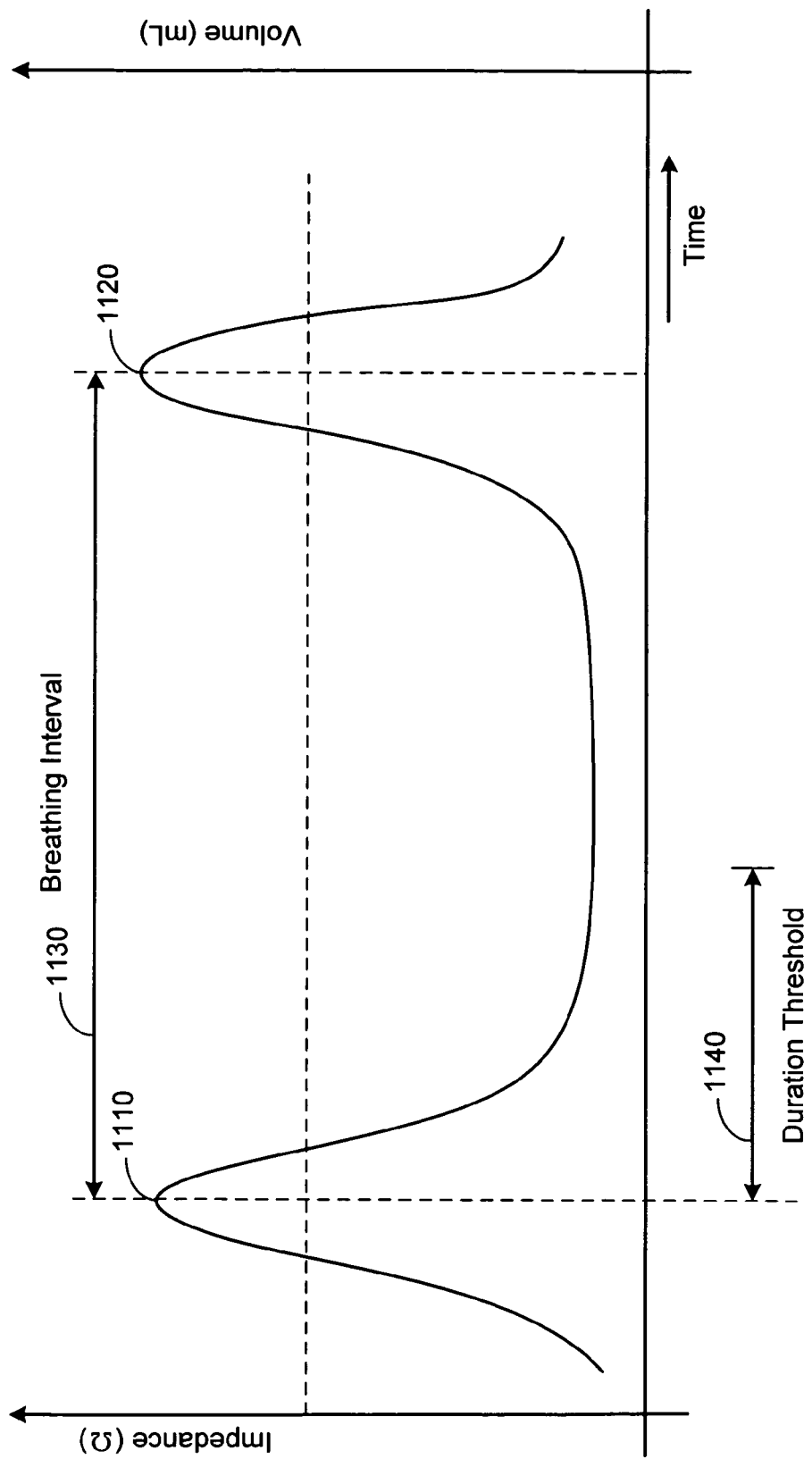
FIG. 11 is a respiration graph illustrating a breath interval utilized in connection with disordered breathing detection in accordance with embodiments of the invention.

According to principles of the invention, a breath interval is established for each respiration cycle. A breath interval represents the interval of time between successive breaths, as illustrated in FIG. 11. A breath interval 1130 may be defined in a variety of ways, for example, as the interval of time between successive maxima 1110, 1120 of the impedance signal waveform.

Detection of disordered breathing, in accordance with embodiments of the invention, involves the establishment of a duration threshold and a tidal volume threshold. If a breath interval exceeds the duration threshold, an apnea event is detected. Detection of sleep apnea, in accordance with this embodiment, is illustrated in the graph of FIG. 11. Apnea represents a period of non-breathing. A breath interval 1130 exceeding a duration threshold 1140 comprises an apnea episode.

Hypopnea may be detected using the duration threshold and tidal volume threshold. A hypopnea event represents a period of shallow breathing. Each respiration cycle in a hypopnea event is characterized by a tidal volume less than the tidal volume threshold. Further, the hypopnea event involves a period of shallow breathing greater than the duration threshold.

Figure 12:
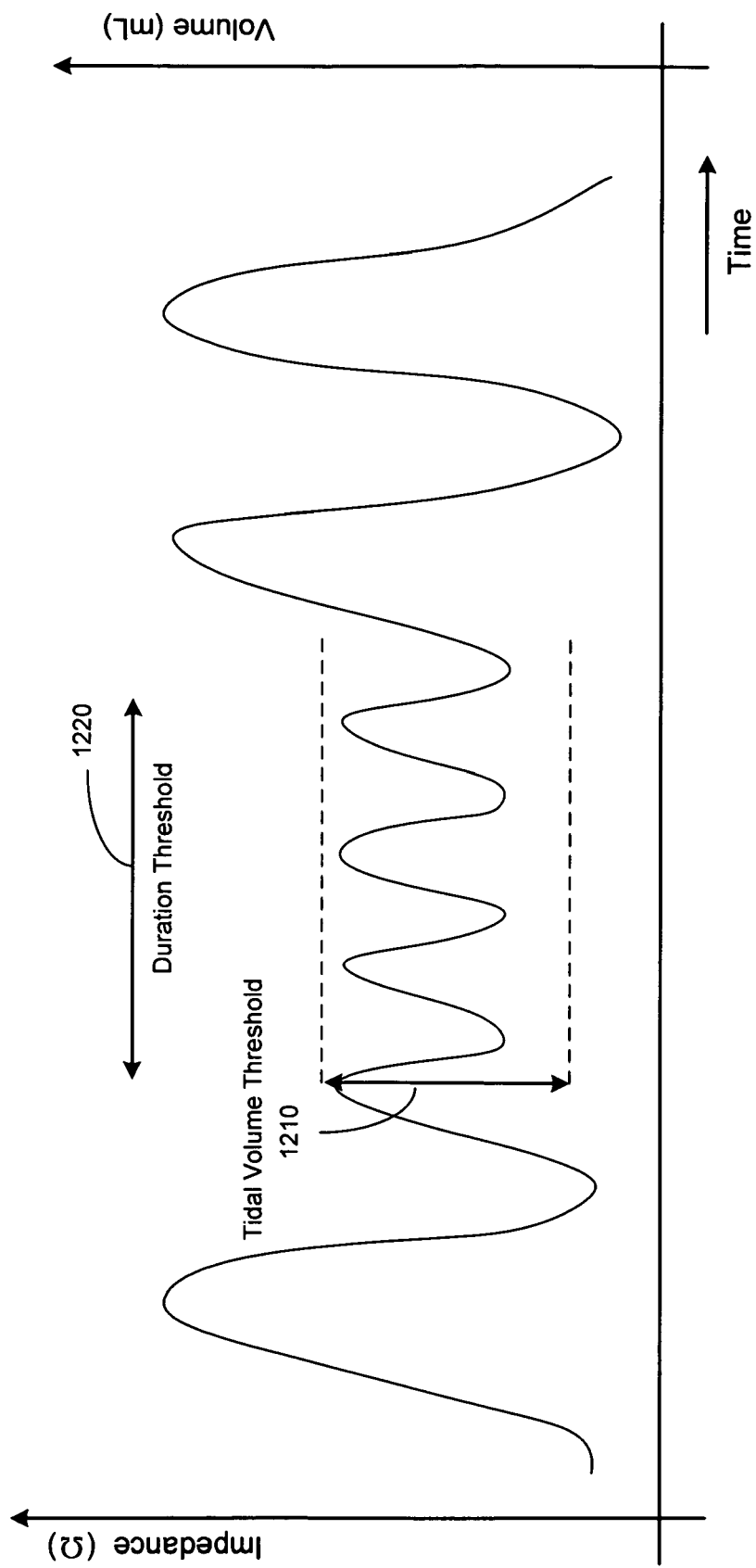
FIG. 12 is a respiration graph illustrating a hypopnea detection approach in accordance with embodiments of the invention.

A hypopnea detection approach, in accordance with embodiments of the invention, is illustrated in FIG. 12. Shallow breathing is detected when the tidal volume of one or more breaths is below a tidal volume threshold 1210. If the shallow breathing continues for an interval greater than a duration threshold 1220, then the breathing pattern represented by the sequence of shallow respiration cycles is classified as a hypopnea event.

Figure 13:
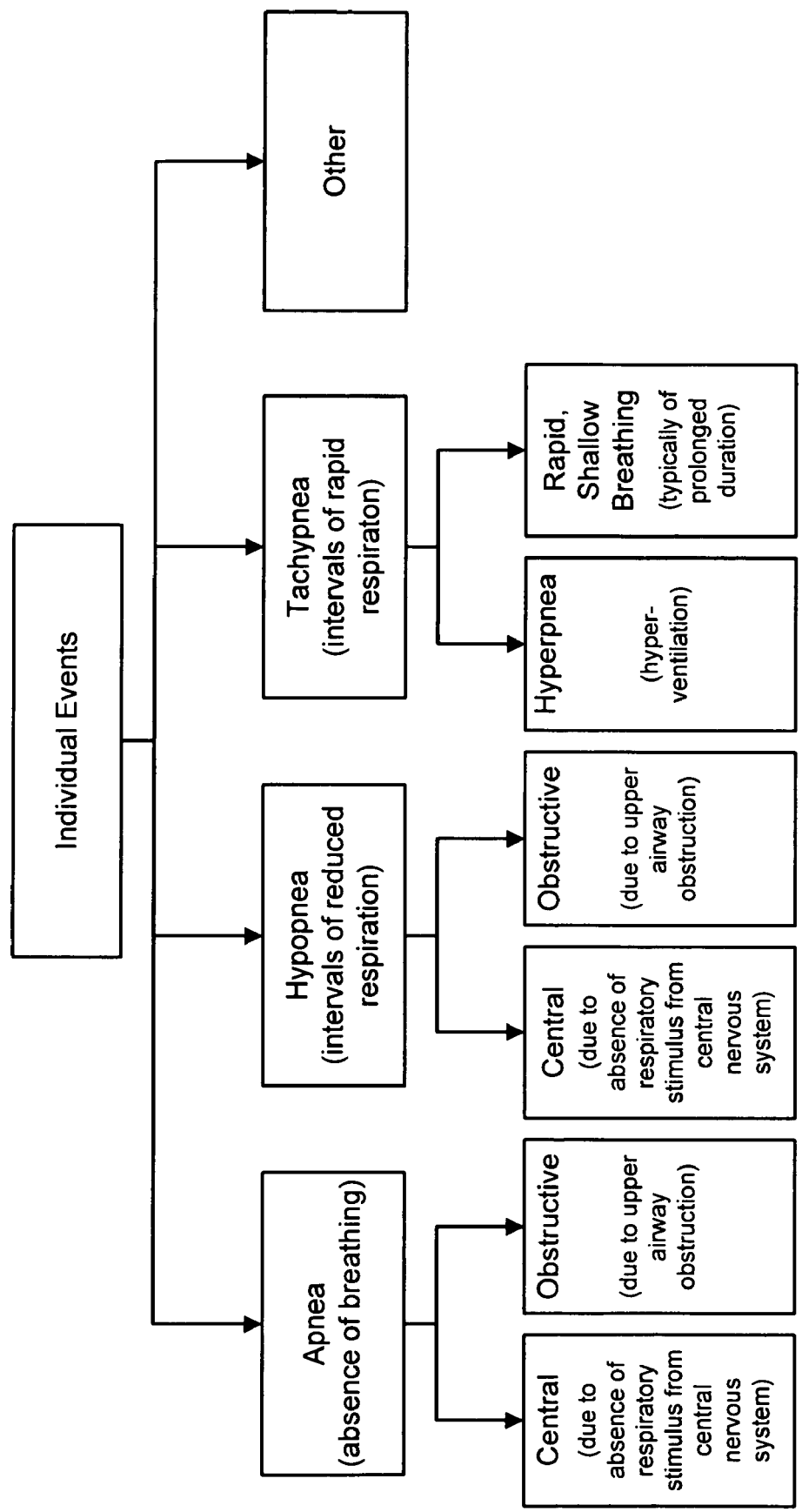
FIGS. 13 and 14 provide charts illustrating classification of individual disordered breathing events and series of periodically recurring disordered breathing events, respectively, in accordance with embodiments of the invention.
Figure 14:
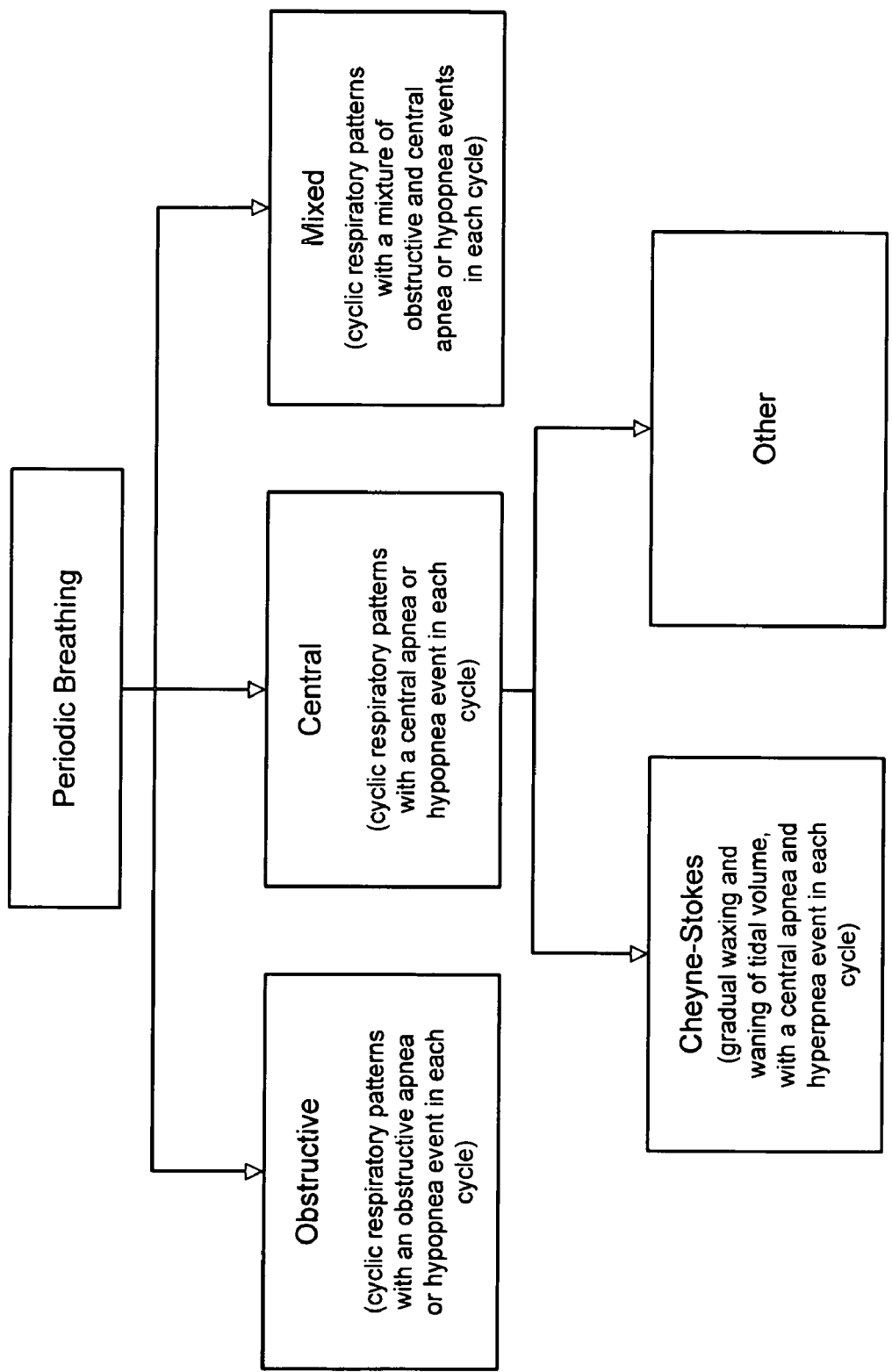

FIGS. 13 and 14 provide charts illustrating classification of individual disordered breathing events and series of periodically recurring disordered breathing events, respectively. As illustrated in FIG. 13, individual disordered breathing events may be grouped into apnea, hypopnea, tachypnea and other disordered breathing events. Apnea events are characterized by a reduction of breathing. Intervals of reduced respiration are classified as hypopnea events. Tachypnea events include intervals of rapid respiration characterized by an elevated respiration rate.

As illustrated in FIG. 13, apnea and hypopnea events may be further subdivided as either central events, related to central nervous system dysfunction, or obstructive events, caused by upper airway obstruction. A tachypnea event may be further classified as a hyperpnea event, represented by hyperventilation, i.e., rapid deep breathing. A tachypnea event may alternatively be classified as rapid breathing, typically of prolonged duration.

FIG. 14 illustrates classification of combinations of periodically recurring disordered breathing events. Periodic breathing may be classified as obstructive, central or mixed. Obstructive periodic breathing is characterized by cyclic respiratory patterns with an obstructive apnea or hypopnea event in each cycle. Central periodic breathing involves cyclic respiratory patterns including a central apnea or hypopnea event in each cycle. Periodic breathing, illustrated in FIG. 15F, may also be of mixed origin. Mixed origin periodic breathing is characterized by cyclic respiratory patterns having a mixture of obstructive and central apnea events in each cycle. Cheyne-Stokes respiration, illustrated in FIG. 15G, is a particular type of periodic breathing involving a gradual waxing and waning of tidal volume and having a central apnea and hyperpnea event in each cycle. Other manifestations of periodic breathing are also possible. The various forms of disordered breathing may be determined based on the characteristic respiration patterns associated with particular types of disordered breathing.

Figure 15A:
FIGS. 15A-E are graphs illustrating respiration patterns that may be classified by origin in accordance with embodiments of the invention.
Figure 15B:
Figure 15C:
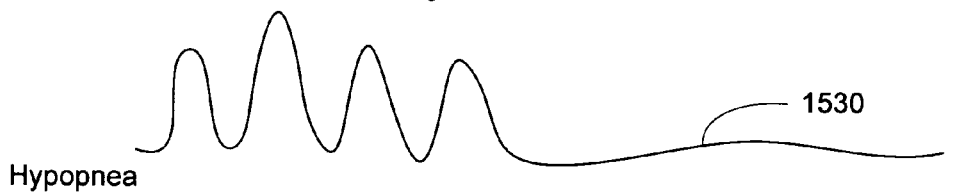
Figure 15D:
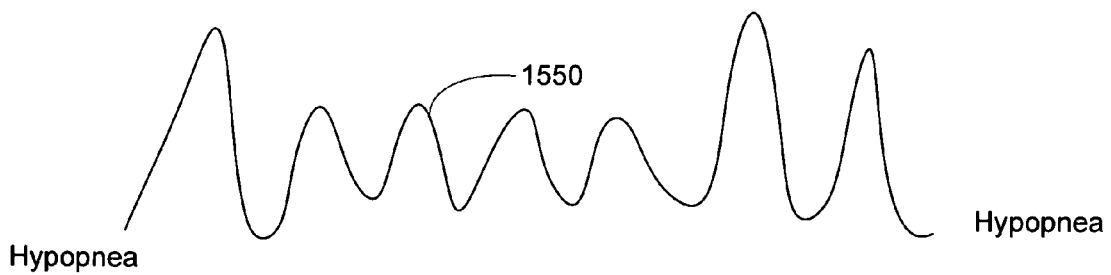
Figure 15E:
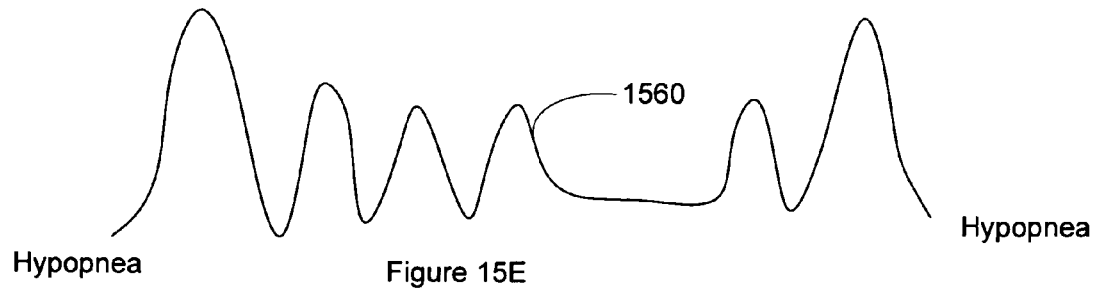
Figure 15F:
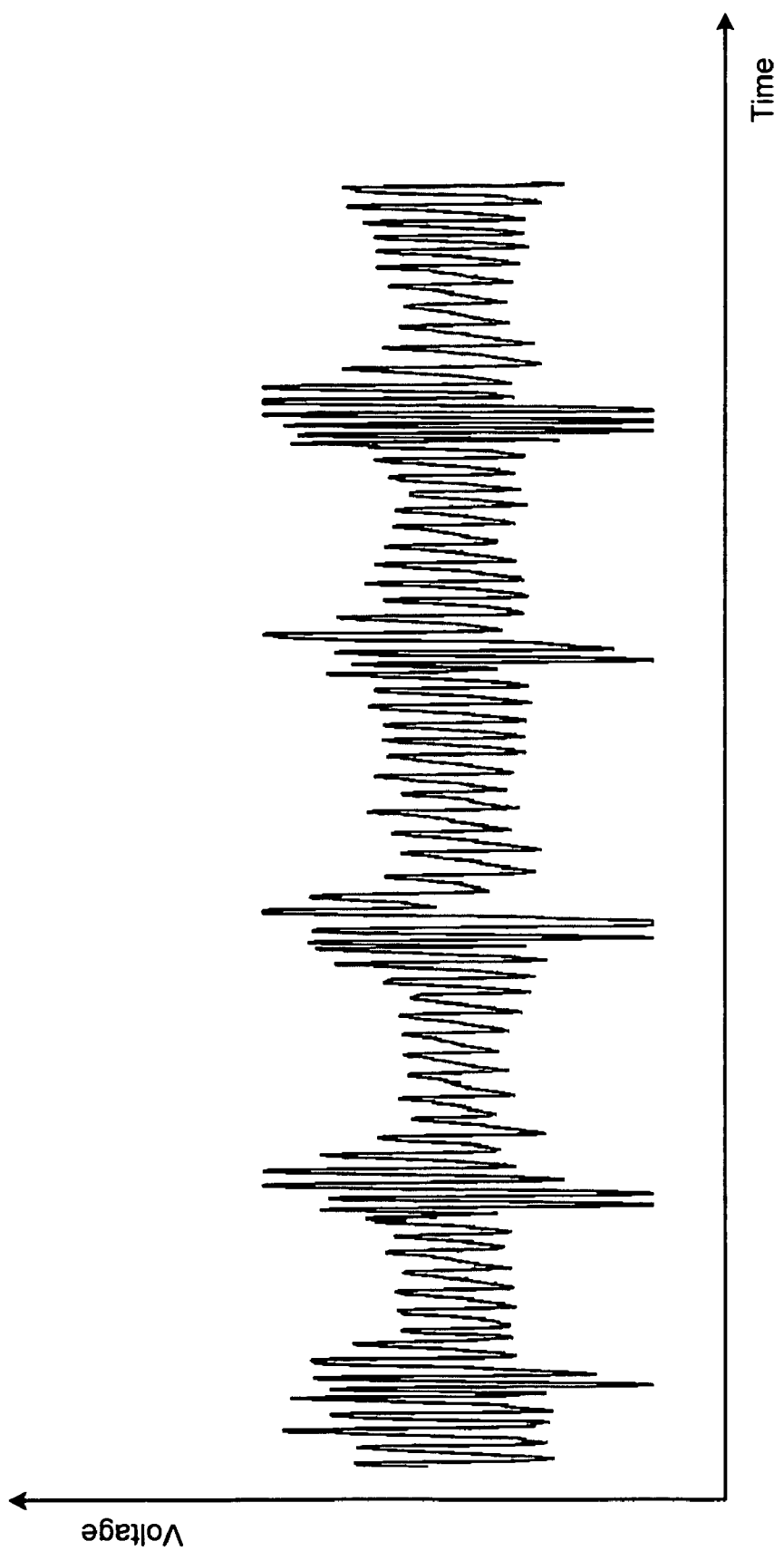
FIG. 15F is a graph illustrating periodic breathing that may be classified with respect to origin in accordance with embodiments of the invention.
Figure 15G:
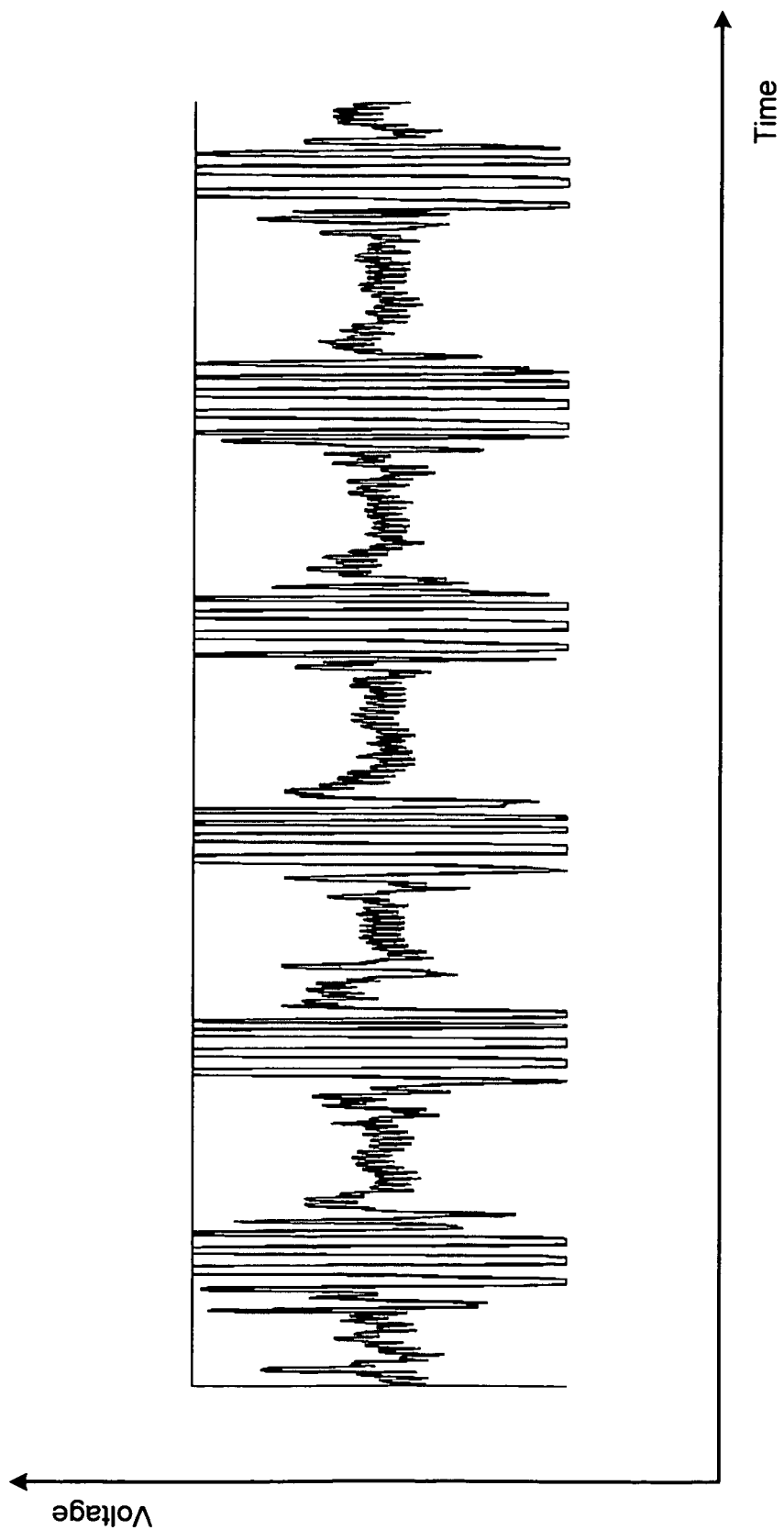
FIG. 15G is a graph illustrating Cheyne-Stokes respiration that may be classified with respect to origin in accordance with embodiments of the invention.

As illustrated in FIGS. 15A-E, a respiration pattern detected as a disordered breathing episode may include only an apnea respiration cycle 1510 (FIG. 15A), only hypopnea respiration cycles 1550 (FIG. 15D), or a mixture of hypopnea and apnea respiration cycles 1520 (FIG. 15B), 1530 (FIG. 15C), 1560 (FIG. 15E). A disordered breathing event 1520 may begin with an apnea respiration cycle and end with one or more hypopnea cycles. In another pattern, the disordered breathing event 1530 may begin with hypopnea cycles and end with an apnea cycle. In yet another pattern, a disordered breathing event 1560 may begin and end with hypopnea cycles with an apnea cycle in between the hypopnea cycles.

Figure 16:
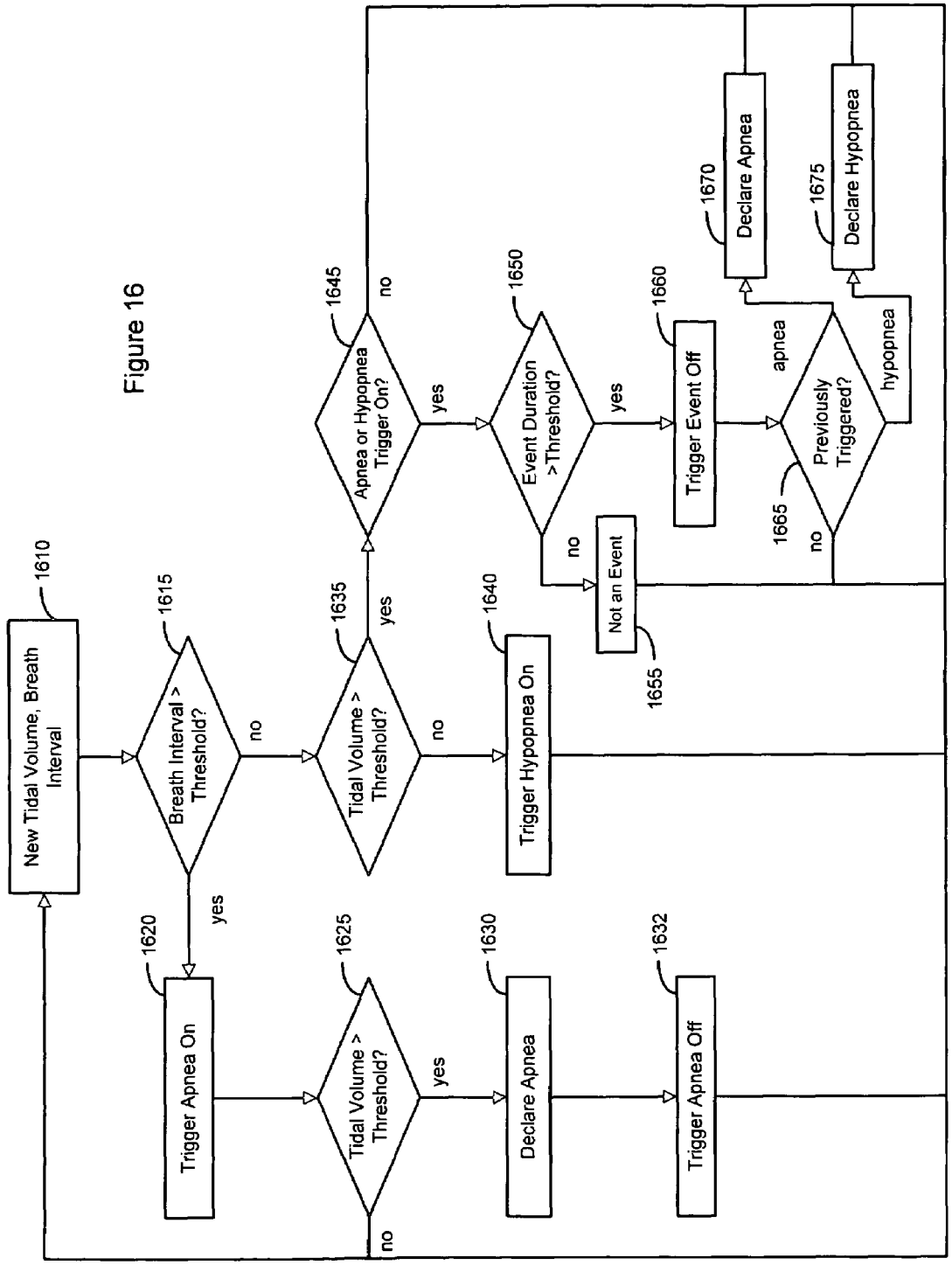
FIG. 16 is a flowchart of a method for detecting disordered breathing in accordance with embodiments of the invention.

FIG. 16 is a flow graph of a method for detecting disordered breathing in accordance with embodiments of the invention. The method illustrated in FIG. 16 operates by classifying breathing patterns using breath intervals in conjunction with tidal volume and duration thresholds as previously described above. In this example, a duration threshold and a tidal volume threshold are established for determining both apnea and hypopnea breath intervals. An apnea episode is detected if the breath interval exceeds the duration threshold. A hypopnea episode is detected if the tidal volume of successive breaths remains less than the tidal volume threshold for a period in excess of the duration threshold. Mixed apnea/hypopnea episodes may also occur. In these cases, the period of disordered breathing is characterized by shallow breaths or non-breathing intervals. During the mixed apnea/hypopnea episodes, the tidal volume of each breath remains less than the tidal volume threshold for a period exceeding the duration threshold.

Transthoracic impedance is sensed and used to determine the patient's respiration cycles. Each breath 1610 may be characterized by a breath interval, the interval of time between two impedance signal maxima, and a tidal volume (TV).

If a breath interval exceeds 1615 the duration threshold, then the respiration pattern is consistent with an apnea event, and an apnea event trigger is turned on 1620. If the tidal volume of the breath interval exceeds 1625 the tidal volume threshold, then the breathing pattern is characterized by two respiration cycles of normal volume separated by a non-breathing interval. This pattern represents a purely apneic disordered breathing event, and apnea is detected 1630. Because the final breath of the breath interval was normal, the apnea event trigger is turned off 1632, signaling the end of the disordered breathing episode. However, if the tidal volume of the breath interval does not exceed 1625 the tidal volume threshold, the disordered breathing period is continuing and the next breath is checked 1610.

If the breath interval does not exceed 1615 the duration threshold, then the tidal volume of the breath is checked 1635. If the tidal volume does not exceed 1635 the tidal volume threshold, the breathing pattern is consistent with a hypopnea cycle and a hypopnea event trigger is set on 1640. If the tidal volume exceeds the tidal volume threshold, then the breath is normal.

If a period of disordered breathing is in progress, detection of a normal breath signals the end of the disordered breathing. If disordered breathing was previously detected 1645, and if the disordered breathing event duration has not exceeded 1650 the duration threshold, and the current breath is normal, then no disordered breathing event is detected 1655. If disordered breathing was previously detected 1645, and if the disordered breathing event duration has extended for a period of time exceeding 1650 the duration threshold, and the current breath is normal, then the disordered breathing trigger is turned off 1660. In this situation, the duration of the disordered breathing episode was of sufficient duration to be classified as a disordered breathing episode. If an apnea event was previously triggered 1665, then an apnea event is declared 1670. If a hypopnea was previously triggered 1665, then a hypopnea event is declared 1675.

Figure 17A:
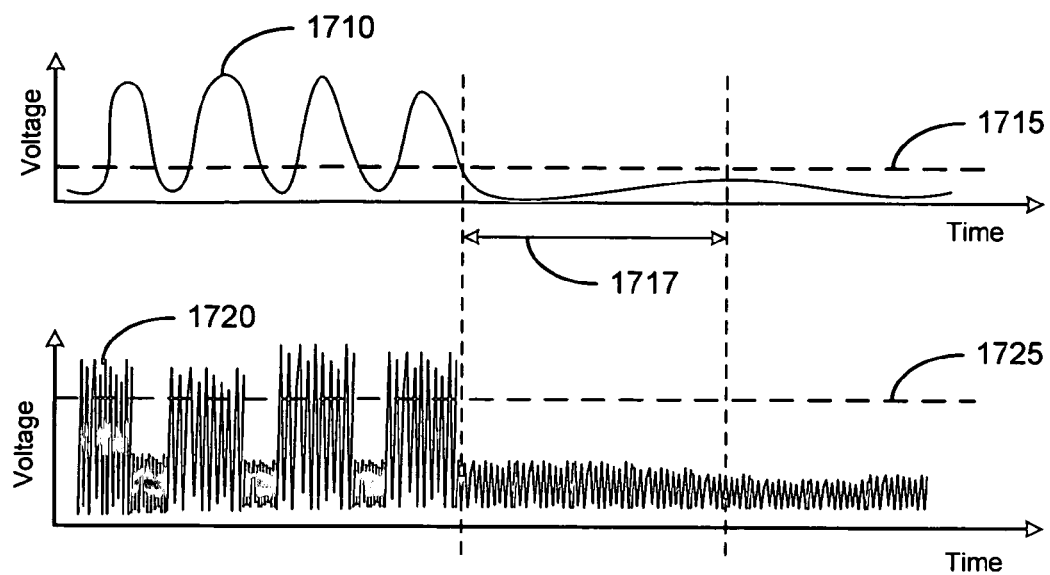
FIGS. 17A and 17B are graphs illustrating representative respiration signals and accelerometer signals associated with chest wall motion for central and obstructive disordered breathing events, respectively, in accordance with embodiments of the invention.
Figure 17B:
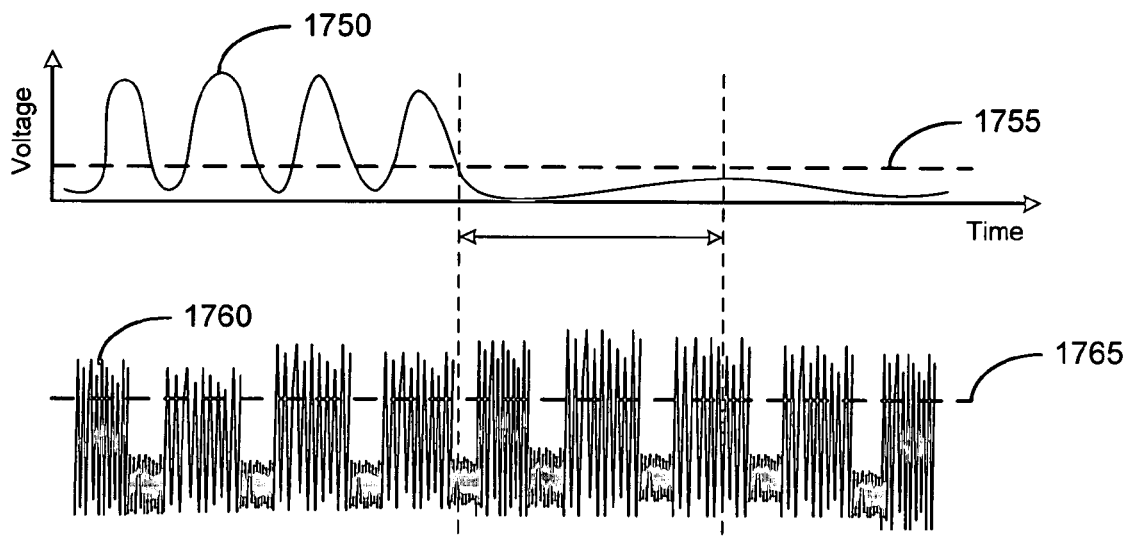

In accordance with various embodiments of the invention a disordered breathing event may be classified as a central disordered breathing event, an obstructive disordered breathing event, or a mixed disordered breathing event comprising both central and obstructive types. Classification of the disordered breathing event by these processes involves evaluating chest wall motion or other motion associated with respiratory effort. FIGS. 17A and 17B provide graphs of accelerometer signals representing chest wall motion for central and obstructive disordered breathing, respectively. As illustrated in FIG. 17A, apnea is detected when the transthoracic impedance signal 1710 remains below an inspiration threshold 1715 for a period of time greater than an apnea interval 1717, e.g., 10 seconds. In this example, the apnea event is a central apnea event and the signal 1720 from an accelerometer sensing the patient's chest wall motion also falls below a motion threshold 1725 during the period of non-respiration. The lack of chest wall motion indicates that the patient's breathing reflex is not being triggered by the central nervous system, indicative of a central disordered breathing event.

FIG. 17B illustrates the accelerometer signal and transthoracic impedance signal for an obstructive apnea event. Apnea is detected when the transthoracic impedance signal 1750 remains below an inspiration threshold 1755 for a period of time greater than an apnea interval 1757. In this example, the apnea event is an obstructive apnea event and the signal 1760 from an accelerometer sensing the patient's chest wall motion rises above a chest well motion threshold 1765 during the period of non-respiration. The chest wall motion indicates that the patient's breathing reflex is being triggered by the central nervous system, indicative of an obstructive disordered breathing event.

Figure 18A:
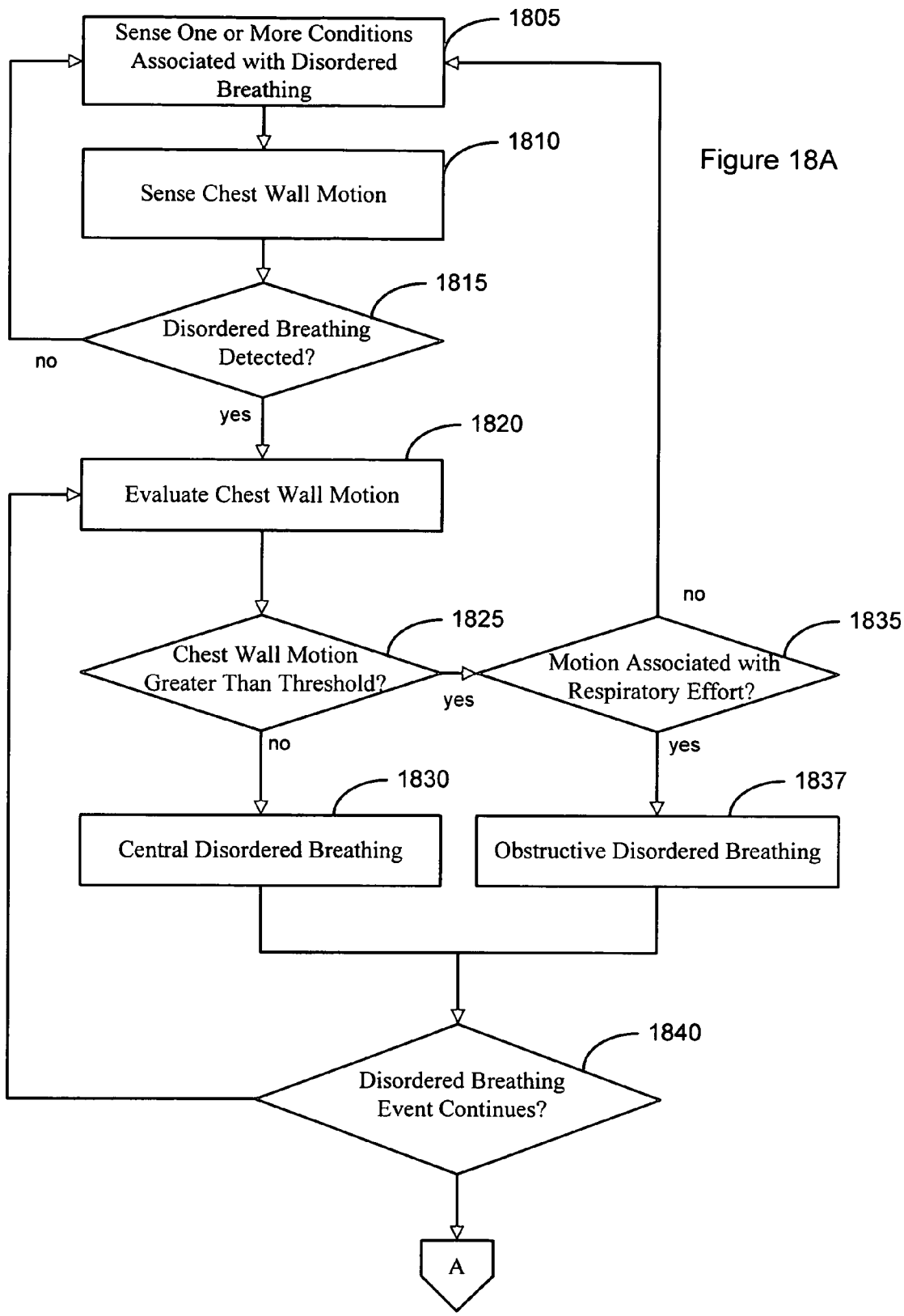
FIGS. 18A and 18B provide a flowchart illustrating a method for classifying a disordered breathing event and using the disordered breathing event classification in accordance with embodiments of the invention.

FIG. 18A is a flowchart of a method for classifying disordered breathing events as central, obstructive or mixed events in accordance with embodiments of the invention. One or more conditions associated with disordered breathing are sensed 1805. For example, one or more of the conditions listed in Table 1 may be sensed to detect that a disordered breathing event is occurring. The patient's chest wall motion is sensed 1810 during the disordered breathing event.

If disordered breathing is detected 1815, then the chest wall motion signals are analyzed 1820 for obstructive/central origin discrimination. A parameter, e.g., average amplitude or frequency, of the signal produced by the motion sensor may be compared to a threshold. If the chest wall motion signal is not greater 1825 than a threshold, then the disordered breathing is classified 1830 as central disordered breathing. If the chest wall motion signal is greater than or equal to the threshold 1825 and the chest wall motion is associated with respiratory effort 1835, then the disordered breathing is classified 1837 as obstructive disordered breathing. For example, if chest wall motion from the accelerometer is synchronous with a reduced transthoracic impedance during a disordered breathing episode, then the concurrence of disordered breathing and chest wall motion indicates disordered breathing that is obstructive in origin.

If the disordered breathing event continues 1840, then chest wall motion continues to be sensed 1820. A second or subsequent portion of the disordered breathing event may have a different classification from the initial classification based on the presence or lack of motion associated with respiratory effort.

Figure 18B:
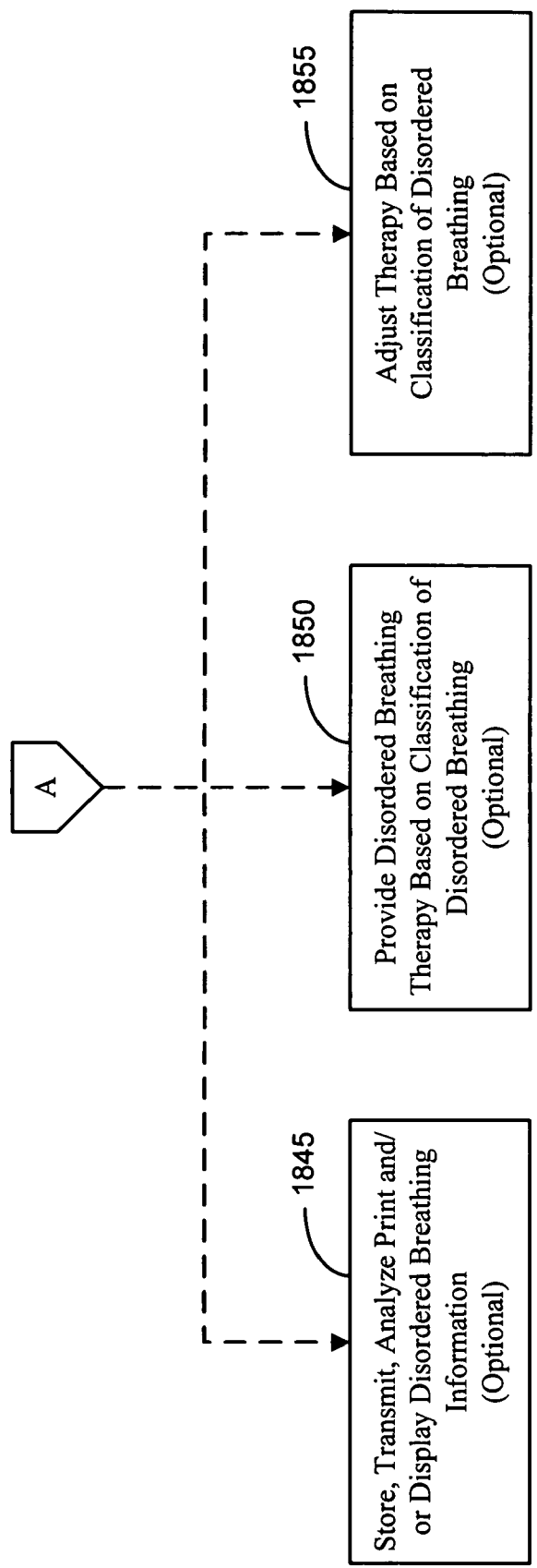

The flowchart of FIG. 18B follows from FIG. 18A and illustrates optional processes that may be implemented following classification of the disordered breathing event. Disordered breathing information may optionally be stored, transmitted, displayed, and/or printed 1845. For example, disordered breathing information may be stored over several weeks or months to enhance diagnosis of disordered breathing or other conditions, or to analyze disordered breathing trends and/or therapy effectiveness.

Additionally, or alternatively, classification of the origin of disordered breathing events may be used in connection with providing 1850 a therapy to treat the disordered breathing. Therapy for treating disordered breathing may involve cardiac pacing therapy, nerve stimulation therapy, respiration therapy such as that provided by an xPAP device, among other therapies. In one scenario, a first therapy may be used to treat disordered breathing that is central in origin. A second therapy may be used to treat disordered breathing that is obstructive in origin. The first and/or the second therapies may be initiated after the origin of the disordered breathing is determined.

Further, therapies other than disordered breathing therapy may be initiated, modified, or terminated 1855 based on the classification of disordered breathing. For example, as previously discussed, disordered breathing in the form of Cheyne-Stokes respiration is related to congestive heart failure and may be used to monitor the progression of CHF. As previously discussed, Cheyne-Stokes respiration is marked by periodic patterns of waxing and waning respiration interrupted by periods of central apnea. Characteristics of the disordered breathing experienced by the patient, e.g., origin, duration, and severity, may be used to initiate or adjust therapy, such as cardiac pacing therapy and/or cardiac resynchronization therapy, delivered to the patient.

In various embodiments of the invention described herein, discrimination between central and obstructive disordered breathing is based on sensing chest wall motion using an implanted motion sensor, e.g., an accelerometer. In other embodiments, a patient-external motion detector, such as a patient-external accelerometer, patient-external respiratory bands, transthoracic impedance sensor, or a mercury switch, may be used alone or in combination with other implanted or patient-external respiratory sensors and detection algorithms for central/obstructive disordered breathing classification.

In one example, a movement sensor, such as an accelerometer, is mounted inside an implantable CRM device to sense chest wall motions that are indicative of obstructive apnea to determine if the sensed chest wall motions are indicative of obstructive apnea. The output of the movement sensor may be used in combination with other sensors (such as trans-thoracic impedance) for classification of obstructive apnea.

Multi-sensor pulse generators are products in a unique position to provide accurate long-term monitoring and prediction of the progression of disease in patients with disordered breathing. Discrimination between types of apnea events provides more accurate diagnosis and monitoring of abnormal respiration patterns associated with CHF or sleep disordered breathing. Monitoring with discrimination between types of apnea may enable therapy improvements to counteract the effects of abnormal respiratory patterns. Cardiac pacing has been used as an effective therapy for disordered breathing. Methods and systems for providing an adaptive cardiac electrical stimulation therapy for disordered breathing are described in commonly owned U.S. Publication No. 2005/0039745, which is incorporated by reference.

Although episodes of disordered breathing can occur when the patient is awake, they most frequently occur during sleep. Sleep detection may be used in concert with discrimination of central and obstructive disordered breathing events for enhanced detection of central and obstructive sleep apnea and/or other forms of disordered breathing. Methods and systems for detecting sleep are described in commonly owned U.S. Pat. No. 7,189,204, which is incorporated by reference.

Methods and systems for detecting REM sleep and/or other sleep states are described in commonly owned U.S. Publication No. 2005/0043652, which is incorporated by reference.

The methods and systems described above provide enhanced disordered breathing discrimination, providing more accurate diagnostic information for disordered breathing. Discrimination between central and obstructive disordered breathing may be particularly useful in connection with monitoring the abnormal breathing patterns of congestive heart failure patients. The improved monitoring may enable therapy improvements to counteract the effect of disordered breathing and/or CHF.

A number of the examples presented herein involve block diagrams illustrating functional blocks used for monitoring functions in accordance with embodiments of the present invention. It will be understood by those skilled in the art that there exist many possible configurations in which these functional blocks can be arranged and implemented. The examples depicted herein provide examples of possible functional arrangements used to implement the approaches of the invention. The components and functionality depicted as separate or discrete blocks/elements in the figures in general can be implemented in combination with other components and functionality. The depiction of such components and functionality in individual or integral form is for purposes of clarity of explanation, and not of limitation. It is also understood that the components and functionality depicted in the Figures and described herein can be implemented in hardware, software, or a combination of hardware and software.

What is claimed is:

1. A method for classifying disordered breathing in a patient, comprising:
   detecting a disordered breathing event;
   sensing motion associated with respiratory effort during the disordered breathing event; and
   classifying the disordered breathing event based on the sensed motion, wherein at least one of detecting, sensing, and classifying is performed at least in part implantably;
   wherein classifying the disordered breathing event comprises classifying the disordered breathing event as a mixed central and obstructive disordered breathing event if the motion associated with respiratory effort is equal to or above a motion threshold during a first portion of the disordered breathing event and the motion associated with respiratory effort is below the motion threshold during a second portion of the disordered breathing event.

2. The method of claim 1, wherein at least two of detecting, sensing, and classifying are performed at least in part implantably.

3. The method of claim 1, wherein all of detecting, sensing, and classifying are performed at least in part implantably.

4. The method of claim 1, wherein the disordered breathing event comprises sleep disordered breathing.

5. The method of claim 1, wherein detecting the disordered breathing event comprises detecting the disordered breathing event based on respiration patterns.

6. The method of claim 1, wherein detecting the disordered breathing event comprises detecting the disordered breathing event based on transthoracic impedance measurements.

7. The method of claim 1, wherein detecting the disordered breathing event comprises detecting the disordered breathing event based on respiratory system conditions.

8. The method of claim 1, wherein sensing the motion associated with respiratory effort during the disordered breathing event comprises sensing chest wall motion associated with the respiratory effort.

9. The method of claim 1, wherein sensing the motion associated with respiratory effort during the disordered breathing event comprises sensing abdominal motion associated with respiratory effort.

10. The method of claim 1, wherein sensing the motion associated with respiratory effort during the disordered breathing event comprises distinguishing the motion associated with respiratory effort from other types of motion.

11. The method of claim 1, wherein classifying the disordered breathing event comprises classifying the disordered breathing event as a central disordered breathing event.

12. The method of claim 1, wherein classifying the disordered breathing event comprises classifying the disordered breathing event as an obstructive disordered breathing event.

13. The method of claim 1, wherein classifying the disordered breathing event comprises classifying the disordered breathing event as an obstructive disordered breathing event if the motion associated with respiratory effort during the disordered breathing event is equal to or above a second motion threshold.

14. The method of claim 1, wherein classifying the disordered breathing event comprises classifying the disordered breathing event as a central disordered breathing event if motion associated with respiratory effort is below a second motion threshold.

15. The method of claim 1, wherein classifying the disordered breathing event comprises discriminating between central disordered breathing and obstructive disordered breathing.

16. The method of claim 1, further comprising storing information associated with the disordered breathing event.

17. The method of claim 1, further comprising transmitting information associated with the disordered breathing event.

18. The method of claim 1, further comprising displaying information associated with the disordered breathing event.

19. The method of claim 1, further comprising using the classification of the disordered breathing event to evaluate disordered breathing trends.

20. The method of claim 1, further comprising delivering a therapy to treat disordered breathing based on the classification of the disordered breathing event.

21. The method of claim 1, further comprising modifying a therapy delivered to the patient based on the classification of the disordered breathing event.

22. The method of claim 21, wherein the modified therapy is a disordered breathing therapy.

23. A system for classifying disordered breathing, comprising:
   a disordered breathing detector configured to detect a disordered breathing event;
   a motion sensor configured to sense motion associated with respiratory effort of a patient during the disordered breathing event; and
   a disordered breathing classification processor coupled to the motion sensor and the disordered breathing detector, the disordered breathing classification processor configured to classify the disordered breathing event based on the respiratory effort motion, wherein at least one of the disordered breathing detector, the motion sensor, and the disordered breathing classification processor is at least in part implantable;
   wherein the disordered breathing classification processor is configured to classify the disordered breathing event as an obstructive disordered breathing event if the motion associated with respiratory effort during the disordered breathing event is equal to or above a motion threshold during a first portion of the disordered breathing event and classify the disordered breathing event as a central disordered breathing event if the motion associated with respiratory effort during the disordered breathing event is below the motion threshold during a second portion of the disordered breathing event.

24. The system of claim 23, wherein at least two of the disordered breathing detector, the motion sensor, and the disordered breathing classification processor are at least in part implantable.

25. The system of claim 23, wherein the disordered breathing detector, the motion sensor, and the disordered breathing classification processor are at least in part implantable.

26. The system of claim 23, wherein the disordered breathing detector comprises a sensor configured to sense patient respiration.

27. The system of claim 26, wherein the respiration sensor comprises a transthoracic impedance sensor.

28. The system of claim 23, wherein the disordered breathing detector comprises a sensor configured to sense respiration system conditions.

29. The system of claim 23, wherein the motion sensor comprises an accelerometer.

30. The system of claim 23, wherein the motion sensor is configured to sense chest wall motion.

31. The system of claim 23, wherein the motion sensor is configured to sense abdominal motion.

32. The system of claim 23, wherein the disordered breathing classification processor is configured to classify the disordered breathing event as a mixed central and obstructive disordered breathing event.

33. The system of claim 23, wherein the disordered breathing classification processor is configured to discriminate between central and obstructive disordered breathing.

34. The system of claim 23, wherein the disordered breathing classification processor is configured to classify the disordered breathing event as an obstructive disordered breathing event if the motion associated with respiratory effort during the disordered breathing event is equal to or above a second motion threshold.

35. The system of claim 23, wherein the disordered breathing classification processor is configured to classify the disordered breathing event as a central disordered breathing event if the motion associated with respiratory effort during the disordered breathing event is below a second motion threshold.

36. The system of claim 23, wherein the disordered breathing classification processor is configured to distinguish between the motion associated with respiratory effort and other types of motion.

37. The system of claim 23, wherein at least one of the motion sensor and the disordered breathing detector is wirelessly coupled to the disordered breathing classification processor.

38. The system of claim 23, wherein at least one of the motion sensor, the disordered breathing detector, and the disordered breathing classification processor is mechanically coupled to a cardiac rhythm management device.

39. The system of claim 23, wherein at least one of the motion sensor, the disordered breathing detector, and the disordered breathing classification processor is mechanically coupled to a positive airway pressure device.

40. The system of claim 23, wherein at least one of the motion sensor, the disordered breathing detector, and the disordered breathing classification processor is coupled to a patient management system.

41. The system of claim 23, further comprising a memory coupled to the disordered breathing classification processor and configured to store information about the disordered breathing event.

42. The system of claim 23, further comprising a display device coupled to the disordered breathing classification processor and configured to display information about the disordered breathing event.

43. The system of claim 23, further comprising a therapy unit coupled to the disordered breathing classification processor and configured to deliver therapy to the patient to treat disordered breathing.

44. The system of claim 23, further comprising a therapy delivery unit coupled to the disordered breathing classification processor and configured to modify a therapy delivered to the patient based on the classification of the disordered breathing event.

45. A disordered breathing classification system, comprising:
   means for detecting a disordered breathing event;
   means for sensing motion associated with respiratory effort during the disordered breathing event; and
   means for classifying the disordered breathing event based on the sensed motion, wherein at least one of the means for sensing, the means for detecting, and the means for classifying is at least partially implantable;
   wherein the classifying means is configured to classify the disordered breathing event as a mixed central and obstructive disordered breathing event if the motion associated with respiratory effort is equal to or above a motion threshold during a first portion of the disordered breathing event and the motion associated with respiratory effort is below the motion threshold during a second portion of the disordered breathing event.

46. The system of claim 45, further comprising means for storing information associated with the disordered breathing event.

47. The system of claim 45, further comprising means for transmitting information associated with the disordered breathing event.

48. The system of claim 45, further comprising means for displaying information associated with the disordered breathing event.

49. The system of claim 45, further comprising means for using the classification of the disordered breathing event to evaluate disordered breathing trends.

50. The system of claim 45, further comprising means for delivering a therapy for disordered breathing based on the classification of the disordered breathing event.

51. The system of claim 45, further comprising means for modifying a therapy delivered to the patient based on the classification of the disordered breathing event.

52. The system of claim 23, wherein the disordered breathing event comprises apnea.

53. The system of claim 23, wherein the disordered breathing detector event comprises hypopnea.

54. A method for classifying disordered breathing in a patient, comprising:
   detecting a disordered breathing event;
   sensing motion associated with respiratory effort during the disordered breathing event; and
   classifying the disordered breathing event based on the sensed motion, wherein at least one of detecting, sensing, and classifying is performed at least in part implantably;
   wherein classifying the disordered breathing event comprises classifying the disordered breathing event as an obstructive disordered breathing event if the motion associated with respiratory effort during the disordered breathing event is equal to or above a motion threshold during a first portion of the disordered breathing event and classifying the disordered breathing event as a central disordered breathing event if the motion associated with respiratory effort during the disordered breathing event is below the motion threshold during a second portion of the disordered breathing event.

55. The method of claim 54, further comprising storing information associated with the disordered breathing event.

56. A system for classifying disordered breathing, comprising:
- a disordered breathing detector configured to detect a disordered breathing event;
- a motion sensor configured to sense motion associated with respiratory effort of a patient during the disordered breathing event; and
- a disordered breathing classification processor coupled to the motion sensor and the disordered breathing detector, the disordered breathing classification processor configured to classify the disordered breathing event based on the respiratory effort motion, wherein at least one of the disordered breathing detector, the motion sensor, and the disordered breathing classification processor is at least in part implantable;
- wherein the disordered breathing classification processor is configured to classify the disordered breathing event as a mixed central and obstructive disordered breathing event if the motion associated with respiratory effort is equal to or above a motion threshold during a first portion of the disordered breathing event and the motion associated with respiratory effort is below the motion threshold during a second portion of the disordered breathing event.

57. The system of claim 56, further comprising a memory coupled to the disordered breathing classification processor and configured to store information about the disordered breathing event.

58. The method of claim 1, wherein the disordered breathing event comprises Cheyne-Stokes respiration.

59. The method of claim 1, wherein the disordered breathing event comprises periodic breathing.

60. The method of claim 1, wherein the disordered breathing event comprises apnea.

61. The method of claim 1, wherein the disordered breathing event comprises hypopnea.

62. The method of claim 1, wherein detecting the disordered breathing event comprises detecting the disordered breathing event based on blood gas level.

63. The method of claim 1, wherein detecting the disordered breathing event comprises detecting the disordered breathing event based on cardiovascular system conditions.

64. The method of claim 1, wherein detecting the disordered breathing event comprises detecting the disordered breathing event based on cardiopulmonary conditions.

65. The method of claim 1, wherein detecting the disordered breathing event comprises detecting the disordered breathing event based on nervous system conditions.

66. The method of claim 1, wherein detecting the disordered breathing event comprises detecting the disordered breathing event based on non-physiological conditions.

67. The system of claim 26, wherein the respiration sensor comprises a microphone configured to detect snoring sounds.

68. The system of claim 26, wherein the respiration sensor comprises an airflow sensor.

69. The system of claim 26, wherein the respiration sensor comprises a sensor configured to sense blood gas.

70. The system of claim 26, wherein the respiration sensor comprises a sensor configured to sense cardiovascular system conditions.

71. The system of claim 23, wherein the disordered breathing detector comprises a sensor configured to sense nervous system conditions.

72. The system of claim 23, wherein the disordered breathing detector comprises a sensor configured to sense muscle system conditions.

73. The system of claim 23, wherein the disordered breathing detector comprises a sensor configured to sense non-physiological conditions.

74. The system of claim 23, wherein the motion sensor comprises a transthoracic impedance sensor.

75. The system of claim 23, wherein the motion sensor comprises a respiratory band.

76. The system of claim 23, wherein the motion sensor comprises a switch.

77. The system of claim 23, wherein the motion sensor comprises an electromyogram sensor.

* * * * *